United States Patent
Shreshtha et al.

(10) Patent No.: US 12,254,538 B2
(45) Date of Patent: Mar. 18, 2025

(54) DEVICES AND PROCESS FOR SYNTHESIZING IMAGES FROM A SOURCE NATURE TO A TARGET NATURE

(71) Applicant: THERAPANACEA, Paris (FR)

(72) Inventors: Kumar Shreshtha, Paris (FR); Aurelien Lombard, Paris (FR); Nikos Paragios, Paris (FR)

(73) Assignee: THERAPANACEA, Paris (FR)

( * ) Notice: Subject to any disclaimer, the term of this patent is extended or adjusted under 35 U.S.C. 154(b) by 356 days.

(21) Appl. No.: 17/576,041

(22) Filed: Jan. 14, 2022

(65) Prior Publication Data
US 2022/0222873 A1 Jul. 14, 2022

(30) Foreign Application Priority Data
Jan. 14, 2021 (EP) ..................................... 21305043

(51) Int. Cl.
*G06T 11/00* (2006.01)
*A61B 34/10* (2016.01)
(Continued)

(52) U.S. Cl.
CPC ............ *G06T 11/008* (2013.01); *A61B 34/10* (2016.02); *G06N 20/20* (2019.01); *G06T 1/20* (2013.01); *G06T 7/0012* (2013.01); *G06T 7/30* (2017.01); *G06T 7/64* (2017.01); *G06V 10/7747* (2022.01); *G16H 30/40* (2018.01);
(Continued)

(58) Field of Classification Search
CPC . G06T 11/008; G06T 7/64; G06T 7/30; G06T 1/20; G06T 7/0012; G06T 2207/10081; G06T 2207/10088; G06T 2207/20081; G06T 2207/20084;
(Continued)

(56) References Cited

U.S. PATENT DOCUMENTS

| 11,756,160 B2* | 9/2023 | Park | G06N 3/048 |
| | | | 382/276 |
| 2019/0392943 A1* | 12/2019 | Sorenson | G16H 50/20 |

(Continued)

OTHER PUBLICATIONS

European Search Report issued Jun. 10, 2021, in corresponding to European Application No. EP21305043, 3 pages.
(Continued)

*Primary Examiner* — Pinalben Patel
(74) *Attorney, Agent, or Firm* — Maier & Maier, PLLC

(57) ABSTRACT

Images are synthesized from a source to a target nature through unsupervised machine learning (ML), based on an original training set of unaligned source and target images, by training a first ML architecture through an unsupervised first learning pipeline applied to the original set, to generate a first trained model and induced target images consisting in representations of original source images compliant with the target nature. A second ML architecture is trained through a supervised second learning pipeline applied to an induced training set of aligned image pairs, each including first and second items corresponding respectively to an original source image and the induced target image associated with the latter, to generate a second trained model enabling image syntheses from the source to the target nature. Also, applications to effective medical image translations.

15 Claims, 16 Drawing Sheets

(51) Int. Cl.
| | |
|---|---|
| *G06N 20/20* | (2019.01) |
| *G06T 1/20* | (2006.01) |
| *G06T 7/00* | (2017.01) |
| *G06T 7/30* | (2017.01) |
| *G06T 7/64* | (2017.01) |
| *G06V 10/774* | (2022.01) |
| *G16H 30/40* | (2018.01) |

(52) U.S. Cl.
CPC ............ *G06T 2207/10081* (2013.01); *G06T 2207/10088* (2013.01); *G06T 2207/20081* (2013.01); *G06T 2207/20084* (2013.01); *G06T 2207/30004* (2013.01)

(58) Field of Classification Search
CPC .......... G06T 2207/30004; A61B 34/10; G16H 30/40; G06N 20/20; G06V 10/7747
See application file for complete search history.

(56) References Cited

U.S. PATENT DOCUMENTS

| | | | |
|---|---|---|---|
| 2020/0027211 A1* | 1/2020 | Dufort | .................... G06N 7/01 |
| 2020/0034948 A1 | 1/2020 | Park et al. | |
| 2023/0342913 A1* | 10/2023 | Patil | ..................... G06T 7/0012 |

OTHER PUBLICATIONS

Bing Cao et al., "Auto-GAN: Self Supervised Collaborative Learning for Medical Image Synthesis"; Proceedings of the AAAI Conference on Artificial Intelligence; vol. 34; No. 7; Jun. 18, 2020; pp. 10486-10493; XP055812407.

Heran Yang et al., "Unsupervised MR-to-CT Synthesis Using Structure-Constrained CycleGAN"; IEEE Transactions on Medical Imaging; IEEE Service Center; vol. 39; No. 12; Aug. 10, 2020; pp. 4249-4261; XP011822949.

* cited by examiner

DEVICES AND PROCESS FOR SYNTHESIZING IMAGES FROM A SOURCE NATURE TO A TARGET NATURE

FIELD

The invention relates to the domain of image synthesis, and regards more particularly medical image modality-to-image modality translation.

BACKGROUND

Image-to-image translation amounts to mapping an image in one domain to a corresponding image in another domain, i.e. from a source domain to a target domain, and has numerous applications in computer vision, image processing and computer graphics. This covers notably super-resolution, image colorization, style transfer, data augmentation and domain adaptation.

In what follows, for sake of convenience and flexibility, the terms image "translation", "generation" and "synthesis" will be used indifferently to refer to transforming an image from a source nature to a target nature.

In the medical field, in particular, translating an image from a source modality to a target modality may prove quite useful, e.g. for generating computed tomography (CT) images from magnetic resonance (MR), ultrasonography (US) or Positron Emission Tomography (PET) images, or conversely.

Focusing for example on the particular case of computed tomography, the latter is essential to clinical domains including diagnostic radiology, interventional radiology, radiation oncology and surgery. In particular, radiation oncology is an area where CT imaging is used for planning purposes (determination of treatment plans) as well as for treatment implementation purposes (i.e. CBCT or MVCT, standing respectively for "Cone Beam CT" and "Megavoltage CT"). This is exploited prior to each session for patient's positioning and treatment adaptation medical decisions.

A main advantage of CT is its ability to offer the necessary information of tissue properties required for dose estimation, while its main limitation is the lack of physiological information along with contrast on soft tissues. This makes multi-parametric magnetic resonance imaging a modality of choice regarding integration of physiological information, as it concerns delineating organs at risks and tumor volumes. Another drawback of CT images relates to its toxicity, since the acquisition itself requires patient irradiation proportional to the quality of image acquisitions, which makes its use for treatment adaptation rather complex in practice.

On the other hand, magnetic resonance imaging (MRI) is an emerging modality in terms of use in radiation therapy. On top of its conventional use for tumor and organ annotation in case of brain tumors for planning, it is now becoming part of the standard CT-based treatment workflow for a number of tumor locations such as breast and prostate. This is due notably to the introduction of MR-Linear accelerators, also called MR-linacs, which combine an MR scanner with a linac (i.e. a linear particle accelerator) in MR-guided radiation therapy. In this respect, instead of using toxic CT related data for patient treatment, MRI is exploited. This increases significantly the ability and interest of adaptive radiation therapy, since high resolution anatomical and functional images can be acquired without additional risks for the patient.

However, in order to determine the optimal dosimetry and the optimal treatment plan, information related to tissue properties are still necessary, which are not present in MR images. This is where constructing synthetic CT images from available MR images may prove quite useful. Existing related methods can be classified into one of three categories: atlas based, segmentation based and learning based.

Atlas-based methods, such as described e.g. J. A. Dowling et al. in "An Atlas-Based Electron Density Mapping Method for Magnetic Resonance Imaging (MRI)-Alone Treatment Planning and Adaptive MRI-Based Prostate Radiation Therapy", *International Journal of Radiation Oncology, Biology, Physics,* 2012, PMID 22330995, use a predefined co-registered MRI-CT pair or multiple such pairs. Synthesis is achieved through a deformable mapping between the target MR sequence of the patient and the ones being part of the predefined database. The recovered deformations are used to deform the paired-CT and product a synthetic CT for the target MR through different consensus strategies. These methods rely heavily on the accuracy of an underlying registration algorithm in generating synthetic CT images.

Image registration, which consists in transforming different sets of data into one coordinate system, may be quite complex as soon as non-rigid (i.e. elastic) transformations are implemented, i.e. where local image warping is allowed, contrasting with linear transformations that are global by nature. This proves particularly challenging when significant anatomical differences exist between the examples of the database and a target volume, or when looking into anatomical areas such as pelvis and abdomen, where intra-patient underlying anatomy is constantly changing over time. Image registration may thus introduce various kinds of alignment or correspondence errors, thereby potentially affecting the precision of the atlas-based methods.

Segmentation-based solutions rely on a different principle, MR images being segmented and MR values being replaced with known CT values per organ. Since they rely heavily on the quality of the semantic segmentation, their reliability is potentially tainted when the variability of the intra and inter organ tissues cannot be properly captured.

The third class of methods, currently particularly popular, defines the challenge of image-to-image translation as a machine learning problem, where a central aspect may consist in generating a matrix of values of a target modality from a matrix of values of a source modality.

Learning-based methods typically use statistical learning techniques to learn a voxel-wise mapping from MRI to CT. Among them, those based on deep fully convolutional neural networks (F-CNN, as described by J. Long, E. Shelhamer and T. Darrell in "Fully Convolutional Networks for Semantic Segmentation", 2015, arXiv: 1411.4038) have gained popularity in recent years and consistently outperformed more conventional technologies. A commonly used or relied-on related machine learning (ML) architecture is known as U-Net and disclosed by O. Ronneberger, P. Fischer and T. Brox in "U-Net: Convolutional Networks for Biomedical Image Segmentation", 2015, arXiv: 1505.04597.

Also, some studies based on convolutional neural networks (CNNs) use adversarial learning techniques to generate sharper and more realistic outputs, generally based on generative adversarial networks (GANs). As developed by I. J. Goodfellow et al. in "Generative Adversarial Networks", 2014, arXiv: 1406.2661, such an ML framework includes two neural networks contesting with each other in a game: a generative network that generates candidates and a discriminative network that evaluates them. It further usually makes use of an adversarial loss or of some variant thereof, in addition to image similarity losses such as L1 distance (taxicab metric using the sum of the absolute differences between values at corresponding Cartesian coordinates) or L2 distance (ordinary Euclidian norm) as exploited in conventional CNN methods. Applications of GANs to medical imaging is e.g. developed by D. Nie et al. in "Medical Image Synthesis with Context-Aware Generative Adversarial Networks", 2016, arXiv: 1612.05362. Also, a popular framework for such image generation relies on a pipeline called pix2pix, which uses GANs conditioned on the input for paired image-to-image translation (conditional GAN), as described by P. Isola et al. in "Image-to-Image translation with Conditional Adversarial Networks", 2018, arXiv: 1611.07004v3.

However, the learning-based methods above require the presence of paired training data, namely a well aligned CT-MRI pair, so that the results heavily depend on the quality of registration of the training data. Obtaining reliable outputs therefore often requires preliminary complex and demanding registration operations, while for many anatomical locations, such alignment is algorithmically challenging (pelvis, abdomen, head and neck, etc.).

To be able to generate synthetic images from training on unpaired data, some authors proposed specific ML algorithms based on unsupervised training. These include Cycle-GAN, as disclosed by J.-Y. Zhu et al. in "Unpaired Image-to-Image Translation using Cycle-Consistent Adversarial Networks", 2020, arXiv: 1703.10593v7, which exploits GAN networks while ensuring cycle consistency. According to the latter, a forward translation from a source domain to a target domain followed by a backward recovery translation from the target domain to the source domain, should stand close to the original value, and the same should apply likewise when translating forth and back from the target domain to the source domain. In practice, the desired similarities are enforced by dedicated cycle consistency losses.

Alternative methods combining variants of GANs and cycle consistency have been elaborated (not necessarily in the medical field), including DiscoGAN as described by T. Kim et al. in "Learning to Discover Cross-Domain Relations with Generative Adversarial Networks", 2017, arXiv: 1703.05192; DualGAN as described by Z. Yi et al. in "DualGAN: Unsupervised Dual Learning for Image-to-Image Translation", 2017, arXiv: 1704.02510; and Harmonic-GAN as developed by R. Zhang; T. Pfister and J. Li in "Harmonic Unpaired Image-to-image Translation", 2019, arXiv: 1902.09727.

Another class of known approaches in image-to-image translation through unsupervised learning relies on the existence of a shared latent space between source and target domains. Related solutions include UNIT, as developed by M.-Y. Liu, T. Breuel and J. Kautz in "Unsupervised Image-to-Image Translation Networks", NIPS 2017, arXiv: 1703.00848; CoGAN (Coupled GAN) as developed by M.-Y. Liu and O. Tuzel in "Coupled Generative Adversarial Networks", NIPS 2016, arXiv: 1606.07536; and MUNIT (Multimodal UNIT) as developed by X. Huang et al. in "Multimodal Unsupervised Image-to-Image Translation", ECCV 2018, arXiv: 1804.04732.

Some alternative technologies, designated in a generic manner as weakly supervised learning, were further elaborated for taking advantage of both supervised and unsupervised method components in image-to-image translation, through combined implementations releasing the supervision constraints. Examples of such implementations include developments by Z. Cao and al. in "Weakly Supervised GAN for Image-to-Image Translation in the Wild", *Mathematical Problems in Engineering*, vol. 2020, Art. ID 6216048, 2020; and by L. Shukla et al. in "Extremely Weak Supervised Image-to-Image Translation for Semantic Segmentation", 2019, arXiv: 1909.08542.

The unsupervised and weakly supervised learning methods may prove particularly efficient for translating MR to CT images. However, the obtained synthetic CT images are still not optimal, and may be of insufficient precision to address specific clinical objectives, such e.g. as dose calculation in the context of radiation therapy. Consequently, there remains room for improvement. In addition, relevant unsupervised or weakly supervised training is generally associated with sophisticated architectures for getting proper image translations. This leads to trained models that are relatively costly in terms of memory and time processing, which may be prejudicial in particular to real-time or near real-time production working.

As apparent to the reader, the above observations made in the specific frame of MRI to CT translations, are also relevant to many other image-to-image translation applications. Notably, in the medical field, the same remarks hold for CT to MRI image translations (e.g. in case of restriction or hindrance conditions with respect to MRI such as cardiac pacemakers, cochlear implants or claustrophobia), or translations involving other modalities among PET, SPECT (standing for "Single-Photon Emission Computed Tomography) or US. Other fields such as e.g. super-resolution, image colorization, style transfer, data augmentation and domain adaptation are also concerned and may face similar challenges.

Consequently, ML implementations enabling to operate on unpaired datasets in achieving image-to-image translation with enhanced achievement performance and/or computing efficiency are desirable and would be highly appreciated.

SUMMARY

A purpose of the present disclosure is a whole category of enhanced ML methods for image-to-image translation, which does not require paired datasets while possibly providing increased overall performance and precision and/or decreased computation costs in production pipelines.

The present disclosure may further apply to various fields of computer vision, image processing and computer graphics, encompassing in particular medical imaging, and more specifically MR to CT translation. In medical imaging, it may be relevant to cross-modality as well as to intra-modality translation (e.g. for turning non-contrast-enhanced CT images to contrast-enhanced CT images).

The present disclosure may further offer such advantages, in some embodiments, subject to limited human intervention, in an automatic or semi-automatic way.

Preliminary Definitions

The terms "adapted" and "configured" are used in the present disclosure as broadly encompassing initial configuration, later adaptation or complementation of the present device, or any combination thereof alike, whether effected through material or software means (including firmware).

The term "processor" should not be construed to be restricted to hardware capable of executing software, and refers in a general way to a processing device, which can for example include a computer, a microprocessor, an integrated circuit, or a programmable logic device (PLD). The processor may also encompass one or more Graphics Processing Units (GPU), whether exploited for computer graphics and image processing or other functions. Additionally, the instructions and/or data enabling to perform associated and/or resulting functionalities may be stored on any processor-readable medium such as, e.g., an integrated circuit, a hard disk, a CD (Compact Disc), an optical disc such as a DVD (Digital Versatile Disc), a RAM (Random-Access Memory) or a ROM (Read-Only Memory). Instructions may be notably stored in hardware, software, firmware or in any combination thereof.

An "image" refers to a visual representation of an object or a scene at a given point of time, or to part of it, whether from the real world or from a virtual world.

The term "image-to-image translation" broadly designates below a task of mapping an image from a source domain to a target domain, while image registration or image alignment stands for transforming different sets of data into a same coordinate system, by spatially transforming a source or moving image to align with a target image.

Image registration is a rigid registration when it preserves distances between points, which includes translations and rotations, by contrast with non-rigid registration; the latter may be based on a linear transformation such as notably an affine transformation (defined as an automorphism of an affine space), which preserves lines and parallelism and notably includes scaling and shear mapping, or may instead be based on a nonlinear transformation, which does not guarantee any distance preservation principle.

An imaging modality refers to a kind of medical technology used for obtaining images, while the nature of images regards more broadly a class of images having common specificities (e.g. level of resolution or of dynamic range, presence or absence of colors, style, etc.), thereby encompassing notably the notion of modality.

In the present disclosure, a source image and a target image are said paired when they are well-aligned, which may depend on the quality of upstream registration. This means that a pair of images may be "paired" or "unpaired".

An atlas of a topological space is classically referring to a family of individual charts (each chart being a coordinate map, consisting in a homeomorphism—topological isomorphism—from an open subset of the topological space to an open subset of a Euclidian space), which describe individual regions of the space and such that the family of charts covers that space (i.e. the union of the open subsets associated with the charts equals the space).

Machine learning (ML) designates in a traditional way computer algorithms improving automatically through experience, on the ground of training data enabling to adjust parameters of computer models through gap reductions between expected outputs extracted from the training data and evaluated outputs computed by the computer models.

Datasets are collections of data used to build an ML mathematical model, so as to make data-driven predictions or decisions. Three types of ML datasets (also designated as ML sets) are typically dedicated to three respective kinds of tasks: training, i.e. fitting the parameters, validation, i.e. tuning ML hyper-parameters (which are parameters used to control the learning process), and testing or evaluation i.e. checking independently of a training dataset exploited for building a mathematical model that the latter model provides satisfying results.

Supervised learning means inferring functions from known input-output examples in the form of labelled training data, exploited by minimizing discrepancies between predicted and known target outputs on the ground of known inputs. This minimization is usually carried out by the means of a similarity cost function, typically based on an L1 or L2 distance. It should be observed that the input-output examples may themselves have been obtained from previous digital processing, and thus be somehow artificial rather than pure monitoring products or empirical data. Also, when combined with unsupervised or weakly supervised aspects further applied to the same input-output examples, the learning is presently still considered as supervised insofar as the overall operations rely on the known input-output examples as defined above.

Unsupervised learning merely refers to non-supervised learning. Consistently with the definition of the supervised mode, the learning is considered as unsupervised insofar as the overall operations do not rely on known input-output examples as specified above. In the present disclosure, this definition also stands for weak supervision, insofar as the latter does not comply with the above-defined stricter supervised learning mode.

Weakly supervised learning is an umbrella term standing for various ML methods involving supervision weakened to some extent, and including notably incomplete supervision (only a subset of training data being provided with labels, which covers active learning and semi-supervised learning), inexact supervision (in which only some coarse supervision information is exploited) and inaccurate supervision (where the supervision information may suffer from errors)—see e.g. the presentation by Z.-H. Zhou in "A Brief Introduction to Weakly Supervised Learning", *National Science Review*, Vol. 5, Issue 1, January 2018, pp. 44-53. In what follows, the weakly supervised learning will be considered consistently with the above definitions of supervised and unsupervised learning, i.e. as generally unsupervised.

Ground truth pertains to information provided by direct observation, thereby constituting empirical data rather than information obtained by inference, even though the ground truth object may be preprocessed or transformed to some extent.

For sake of convenience, in the present disclosure, a distinction is made in ML between an ML architecture, which refers to a specific set of arranged functionalities defining ML methods, and a learning pipeline, which designates a set of instructions for executing learning operations corresponding to a given ML architecture, and typically involves one or more cost functions. Namely, a same ML architecture may possibly be exploited with various learning pipelines, one of which may e.g. be supervised and another unsupervised.

An image to image translation between two domains is bidirectional when it allows for generation of images from one domain to the other in both directions.

Cycle consistency of an image translation from a source domain to a target domain amounts to ensuring that successive forward and backward translation between the source and the target domains keep similar value, in either direction (bidirectional working). The desired similarities are usually enforced by dedicated cycle consistency or reconstruction losses.

A deterministic algorithm in the present context is an algorithm from a first domain to a second domain that, for a given image of the first domain, always generates a same image of the second domain.

An ensemble model is an ML model that uses multiple instances of same or different ML algorithms to obtain better predictive performance than the constituent ML algorithms taken alone.

A neural network or artificial neural network (ANN) designates a category of ML comprising nodes (called neurons), and connections between neurons modeled by weights. For each neuron, an output is given in function of an input or a set of inputs by an activation function. Neurons are generally organized into multiple layers, so that neurons of one layer connect only to neurons of the immediately preceding and immediately following layers.

A Deep Neural Network (DNN) is an ANN comprising multiple layers (called hidden layers) between an input layer and an output layer.

Sigmoid activation functions, i.e. having a S-shaped curve (such as notably the logistic function) are commonly exploited for ANNs having a finite interval domain. Also, several particular activation functions are commonly exploited for increasing nonlinear properties of an ANN network. They notably concern a Rectified Linear Unit (ReLU, or ramp function), which is an ANN unit outputting the positive part of the argument of an input value; a Leaky ReLU, which further provides for a small positive gradient associated with the negative part (such as a slope of 0.01); and the hyperbolic tangent (tanh).

A Convolutional Neural Network (CNN) is a class of DNN, in which the hidden layers convolve (cross-correlation) with a multiplication or other dot product, each convolutional neuron processing input data only from a restricted subarea of a previous layer, called a receptive field. It usually includes a fully connected layer (i.e. in which neurons have connections to all activations in the previous layer) as the output layer. The activation function of a convolutional neuron is determined by a filter consisting in a vector of weights and a bias. A convolutional layer has a kernel, specified by a width and a height defining a tiling region of an input feature map (or of an image for the input layer), and a depth equal to a number of channels of the input feature map; a stride further controls a length of kernel translations in the spatial dimensions (i.e. width and height) when providing the output of a convolutional layer (hence hyper-parameters: width×height×depth, stride).

A Fully Convolutional Neural Network (F-CNN) is a usual contracting network supplemented by successive convolutional layers, where the final convolution layers are followed by an upsampling operation, so that those layers increase the resolution of the output, the input and the output having same spatial dimensions (the F-CNN thereby not needing any fully connected layer). Upsampling may notably be obtained by transposed convolution layers, which rely on transposed convolution matrices and for which the kernel filters can be learned (same connectivity as a normal convolution but in the backward direction).

A U-Net is built upon an F-CNN by extending the related architecture with an upsampling part having a large number of feature channels, and thereby providing a u-shaped architecture comprising a contracting path (encoder that provides downsampling) similar to a usual CNN and an expansive path (decoder that provides upsampling) more or less symmetric thereto. Skip connections are further provided between the contracting path and the expansive path, allowing the network to propagate context information to higher resolution layers.

A generative ML model involves a statistical model of a joint probability distribution on an observable variable and a target variable (which amounts to uncovering underlying causal relationships between both), which may be a deep generative model (DGM) combining a generative model and a DNN, while a discriminative ML model refers to a conditional probability of a target variable given an observation, or to classification computations without probability model (which amounts to learning a predictor given an observation).

A Generative Adversarial Network (GAN) is a DGM involving two ANNs contesting with each other (in terms of data distribution), which enables to generate new data from a given training set by learning: one of the ANNs, called a generative network, generates candidates, while the other ANN, called a discriminative network, evaluates them. Accordingly, the quality of generated images improves as the generative and discriminative networks compete to reach a Nash equilibrium, expressed by the minimax loss of a training process and usually represented by an adversarial loss.

An autoencoder is an ANN learning to copy its input to its output via an internal (hidden) layer that describes a code representing the input, and which comprises an encoder mapping the input into the code, and a decoder mapping the code to a reconstruction of the input.

A variational autoencoder (VAE) is a DGM autoencoder, in which the encoder corresponds to a recognition model and the decoder corresponds to a generative model relying on a directed probabilistic graphical model, and which uses a variational approach for latent representation learning.

A similarity consists in the identification of equivalence relationships between objects based on a similarity measure (i.e. a real-valued function that quantifies the similarity between two objects) applied to couples of objects.

The ML terminology and definitions are compliant with their most up-to-date usual meaning (except where stated otherwise), and can be completed with numerous associated features and properties, well known to a person skilled in the ML field.

Additional terms will be defined, specified or commented wherever useful throughout the following description.

Objects of the Disclosure

An object of the present disclosure is notably a device for synthesizing images from a source nature to a target nature through unsupervised machine learning, on the basis of an original training set of unaligned original source images compliant with the source nature and original target images compliant with the target nature. The device comprises:
- at least one input adapted to receive the original training set,
- at least one processor configured for training a first machine learning architecture through an unsupervised first learning pipeline applied to the original training set, so as to generate a trained model of the first machine learning architecture, adapted to receive images compliant with the source nature and to yield respectively associated images compliant with the target nature, and representations of a plurality of the original source images compliant with the target nature, called induced target images.

According to the disclosure, the processor(s) is/are configured for training a second machine learning architecture through an at least partly supervised second learning pipeline applied at least to an induced training set of aligned image pairs, each of those aligned image pairs comprising a first item corresponding to one of the original source images, called a kept source image, and a second item corresponding to the induced target image associated with that kept source image, so as to generate a trained model of the second machine learning architecture, adapted to receive images compliant with the source nature and to yield respectively associated images compliant with the target nature.

The device further comprises at least one output adapted to produce at least part of the trained model of the second machine learning architecture, so as to carry out image syntheses from the source nature to the target nature.

According to one preferred embodiment, the present disclosure relates to a device for synthesizing images from a source imaging modality to a target imaging modality through unsupervised machine learning, on the basis of an original training set of unaligned original source images compliant with the source imaging modality and original target images compliant with the target imaging modality. The device comprises:
- at least one input adapted to receive the original training set,
- at least one processor configured for training a first machine learning architecture through an unsupervised first learning pipeline applied to the original training set, so as to generate a trained model of the first machine learning architecture, adapted to receive images compliant with the source imaging modality and to yield respectively associated images compliant with the target imaging modality, and representations of a plurality of the original source images compliant with the target imaging modality, called induced target images.

According to this preferred embodiment, the processor(s) is/are configured for training a second machine learning architecture through an at least partly supervised second learning pipeline applied at least to an induced training set of aligned image pairs, each of those aligned image pairs comprising a first item corresponding to one of the original source images, called a kept source image, and a second item corresponding to the induced target image associated with that kept source image, so as to generate a trained model of the second machine learning architecture, adapted to receive images compliant with the source imaging modality and to yield respectively associated images compliant with the target imaging modality.

According to this preferred embodiment, the device further comprises at least one output adapted to produce at least part of the trained model of the second machine learning architecture, so as to carry out image syntheses from the source imaging modality to the target imaging modality.

The device according to the disclosure is thus basically relying on an overall unsupervised learning approach. However, contrary to related usual expectations and by contrast with existing unsupervised or weakly supervised methods, the exploited product of the unsupervised learning is not the trained model yielded by iteratively setting parameters such as weights and biases on the basis of a reference training dataset, the latter being then disregarded in following production operations or merely considered as upgraded to enhanced ancillary data. On the contrary, the trained model obtained in a first stage may itself be possibly disregarded, while the kept useful information relies on a modified training dataset involving the induced target images.

The presence of the second phase is thus decisive, and it strongly relies on the modified training dataset. Indeed, the latter enables to build a new training dataset of image pairs (the induced training set) that are potentially endowed with better quality alignment, which is then exploited in a supervised learning process so as to produce the effective trained model that is later used in production operations. Given the way the induced target images are generated, from a transformation of the original source images towards the target nature, they may be at least substantially aligned with those original source images. They are thereby proper to build the induced training set of the aligned image pairs, which may or may not be identical or similar to the modified training set including the original source images and the induced target images. Namely, some further transformations or modifications may be carried out. In particular, still surprisingly given the usual practice, some features of the original target images may be reinjected in constructing the induced training set (into the second items of the aligned image pairs).

The present device can thus be considered as relying on an ensemble model including an unsupervised constituent and a supervised constituent, and globally working as a self-supervised scheme. The skilled person will appreciate the significant potentialities offered by this category of achievements. In particular, substantial performance enhancement may be obtained with respect to a mere usual unsupervised learning process, thanks to the refinement provided by the second phase (supervised), specially where features of the original target images are reinjected into the induced training set. Also, substantial computing efficiency in production may be gained by properly generating the trained model of the second phase (supervised), whatever the complexity of the trained model of the first phase (unsupervised). Those advantages pertaining to the potential reliability and precision of the effective trained model and to computing efficiency may further cumulate in some embodiments.

According to an attractive branch of implementations, the original training set includes unaligned image pairs of the original source and target images. The processor(s) is/are further configured for training the first machine learning architecture through the first learning pipeline by jointly dealing with the original source and target images of each of the unaligned image pairs, and for generating the second item of one or more (possibly all) of the aligned image pairs associated with one of the original source images belonging to one of those unaligned image pairs by aligning the original target image associated with the original source image to the induced target image associated with the original source image.

This category of embodiments makes strongest use of reinjection operations into the induced training set based on the original target images, between the first phase and the second phase. More precisely, though the image pairs of the original training set are unaligned, the associated source and target images correspond at least to some extent, i.e. are weakly aligned (e.g. medical images of same organ of same patient obtained from two distinct modalities), so that jointly dealing with the original source and target images in the first phase may make sense in terms of output performance and/or computation efficiency.

Also, aligning the original target image to the induced target image in constituting the induced training set with a view to the second training phase may enable to substantially reinforce the content relevance of the target images in the induced training set, while keeping the source-target image alignment gained from the first training phase. In this respect, the supervised learning of the second learning pipeline may then rely on ground truth target images in the induced training set, which have the further favorable property of being completely or at least substantially aligned in pairs with the source images of the latter set.

According to another attractive branch of implementations, which may be combined with the previous branch, the second machine learning architecture is more efficient than the first machine learning architecture in a production phase.

The efficiency refers to the computation costs, which may be in terms of time and/or memory and/or of required resources, e.g. complexity of electronic circuits. This efficiency is reflected in the nature and constitution of the ML architecture.

It deserves noting that the production phase may possibly rely on only part of the second ML architecture once the trained model is acquired, notably keeping only the forward direction in a cycle consistent implementation (e.g. in a CycleGAN architecture) and disregarding the backward direction.

In particular embodiments of such implementations, the first and second ML architectures comprising weights and biases, the second ML architecture is similar to the first ML architecture, subject to a reduction of numbers of those weights and biases.

The first and second ML architectures may e.g. have similar U-Net configurations with corresponding convolutional layers, but with the second ML architecture having reduced numbers of filters in all those layers compared with the first ML architecture (possibly with a same proportionality factor).

In some modes, the first ML architecture and the first learning pipeline are together bidirectional and cycle consistent.

Namely, the functionalities of the related model take account of image transformations in both directions (from either domain to the other) while providing the potential for cycle consistency, and the effective learning pipeline builds on those functionalities—typically through cost function minimization.

In particular modes, the second ML architecture is suited to unsupervised learning and the second learning pipeline involves a joint minimization of at least one term representative of that unsupervised learning and at least one term representative of mismatches between the aligned image pairs and intermediate approximations of those aligned image pairs in the joint minimization.

According to the above-specified terminology, though involving mixed supervised-unsupervised operations, the second phase remains overall supervised since it relies on minimizing dissimilarities between predictions and predetermined data belonging to the training set (i.e. the induced training set).

The introduction of unsupervised aspects in the second phase may prove particularly interesting, by enhancing the effective trained model and thereby getting still better results in the production phase.

In more specific implementations, the second ML architecture and the second learning pipeline are together bidirectional and cycle consistent.

Having both first phase and second phase cycle consistent may prove particularly relevant to the reliability and precision of the production results.

In some embodiments, the trained models generated by training the first and second ML architectures are deterministic.

Potential variations in obtained images are thus turned down, insofar as for a given input image, different outputs may otherwise be got on each run of the concerned algorithms. For example, in the present embodiments, test time dropouts or random noise seeds, which allow to introduce randomness to the framework, are excluded. This unequivocal correspondence between images may prove particularly desirable in medical imaging applications.

In some modes, each of the first and second ML architectures includes at least one generative adversarial network comprising a generator network based on a fully convolutional network.

In particular embodiments, the processor(s) is/are configured for preprocessing the original training set by commonly registering the original source and target images to at least two reference image spaces, independently training the first ML architecture on those respective reference image spaces so as to obtain instances of the induced target images associated with those respective reference image spaces, and combining those instances into the induced target images.

This provides an ensemble strategy that may mitigate data variability, in reducing artifacts present in the reference images spaces thanks to the reconstruction combination. This advantageous property may be obtained due to inconsistencies between artifacts in the respective reference images spaces.

In advantageous related implementations, the common registering is affine. Also, in advantageous medical applications, the reference image spaces are body atlases.

In other particular embodiments, which may be combined with the previous ones, the original source and target images are defined in an overall image space comprising at least two image subspaces, the latter being selected among channel spaces and multidimensional spaces. The processor(s) is/are then configured for training the first ML architecture on those image subspaces corresponding to the original training set, so as to obtain instances of the induced target images respectively associated with the image subspaces, combining those instances into the induced target images, and training the second ML architecture on a reduced number of the image subspaces corresponding to the induced training set.

This provides an ensemble strategy that like in the previous embodiments, may mitigate data variability, in reducing artifacts present in the image subspaces thanks to the reconstruction combination. In addition, using a reduced number of the image subspaces may increase the processing efficiency of the second phase, and consequently of the overall process, without jeopardizing the quality of the results. Indeed, the second phase involves stronger supervised constraints guiding the objective compared with the first phase, which may lead to minimal artifacts.

In advantageous medical applications, each of the image subspaces corresponds to 2D slices of volumes according to a given view, e.g. axial, sagittal or coronal.

In some applications, the images being medical images, one of the source nature and the target nature is MRI and the other is CT imaging.

The disclosure also relates to a device for treatment planning comprising a device for translating medical images, in which the latter is a device for synthesizing images as above, adapted to translate MR images to CT images. The device for treatment planning comprises:
- at least one input adapted to receive operational MR images, the device for synthesizing being adapted to translate the latter to synthetic CT images,
- at least one processor configured for automatically contouring organs in those synthetic CT images,
- at least one output adapted to produce organ contours from that contouring with a view to radiation dose delivery.

The performance of automatic contouring of organs is particularly important since it impacts the dose delivery in adaptive treatment planning, and this depends on the quality of the exploited synthetic CT images. The device for treatment therefore builds on the device for synthesizing according to the disclosure, which may possibly provide high quality induced CT images.

In advantageous implementations, the device for treatment is further adapted to determine organ tissue properties, with a view to simulate the impact of radiation dose delivery.

Another object of the disclosure is a method for synthesizing images from a source nature to a target nature through unsupervised machine learning, on the basis of an original training set of unaligned original source images compliant with the source nature and original target images compliant with the target nature. The method comprises:
- receiving the original training set,
- training by at least one processor a first machine learning architecture through an unsupervised first learning pipeline applied to the original training set, so as to generate a trained model of the first machine learning architecture, adapted to receive images compliant with the source nature and to yield respectively associated images compliant with the target nature, and representations of a plurality of said original source images compliant with the target nature, called induced target images.

According to the disclosure, the method comprises training by the processor(s) a second machine learning architecture through an at least partly supervised second learning pipeline applied at least to an induced training set of aligned image pairs, each of the aligned image pairs comprising a first item corresponding to one of the original source images, called a kept source image, and a second item corresponding to the induced target image associated with that kept source image, so as to generate a trained model of the second machine learning architecture, adapted to receive images compliant with the source nature and to yield respectively associated images compliant with the target nature.

The method further comprises producing at least part of the trained model of the second machine learning architecture, so as to carry out image syntheses from the source nature to the target nature.

The method for synthesizing is advantageously executed by a device for synthesizing according to any of the embodiments of the disclosure.

In addition, the disclosure relates to a computer program comprising software code adapted to perform a method for synthesizing according to the disclosure when it is executed by a processor.

The present disclosure further pertains to a non-transitory program storage device, readable by a computer, tangibly embodying a program of instructions executable by the computer to perform a method for synthesizing compliant with the present disclosure.

Such a non-transitory program storage device can be, without limitation, an electronic, magnetic, optical, electromagnetic, infrared, or semiconductor device, or any suitable combination of the foregoing. It is to be appreciated that the following, while providing more specific examples, is merely an illustrative and not exhaustive listing as readily appreciated by one of ordinary skill in the art: a portable computer diskette, a hard disk, a ROM, an EPROM (Erasable Programmable ROM) or a Flash memory, a portable CD-ROM (Compact-Disc ROM).

BRIEF DESCRIPTION OF THE DRAWINGS

The present disclosure will be better understood, and other specific features and advantages will emerge upon reading the following description of particular and non-restrictive illustrative embodiments, the description making reference to the annexed drawings wherein.

On the figures, the drawings are not to scale, and identical or similar elements are designated by the same references.

DETAILED DESCRIPTION

The present description illustrates the principles of the present disclosure. It will thus be appreciated that those skilled in the art will be able to devise various arrangements that, although not explicitly described or shown herein, embody the principles of the disclosure and are included within its spirit and scope.

All examples and conditional language recited herein are intended for educational purposes to aid the reader in understanding the principles of the disclosure and the concepts contributed by the inventor to furthering the art, and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

Thus, for example, it will be appreciated by those skilled in the art that the block diagrams presented herein may represent conceptual views of illustrative circuitry embodying the principles of the disclosure. Similarly, it will be appreciated that any flow charts, flow diagrams, and the like represent various processes which may be substantially represented in computer readable media and so executed by a computer or processor, whether or not such computer or processor is explicitly shown.

The functions of the various elements shown in the figures may be provided through the use of dedicated hardware as well as hardware capable of executing software in association with appropriate software. When provided by a processor, the functions may be provided by a single dedicated processor, a single shared processor, or a plurality of individual processors, some of which may be shared.

It should be understood that the elements shown in the figures may be implemented in various forms of hardware, software or combinations thereof. Preferably, these elements are implemented in a combination of hardware and software on one or more appropriately programmed general-purpose devices, which may include a processor, memory and input/output interfaces.

Figure 1:
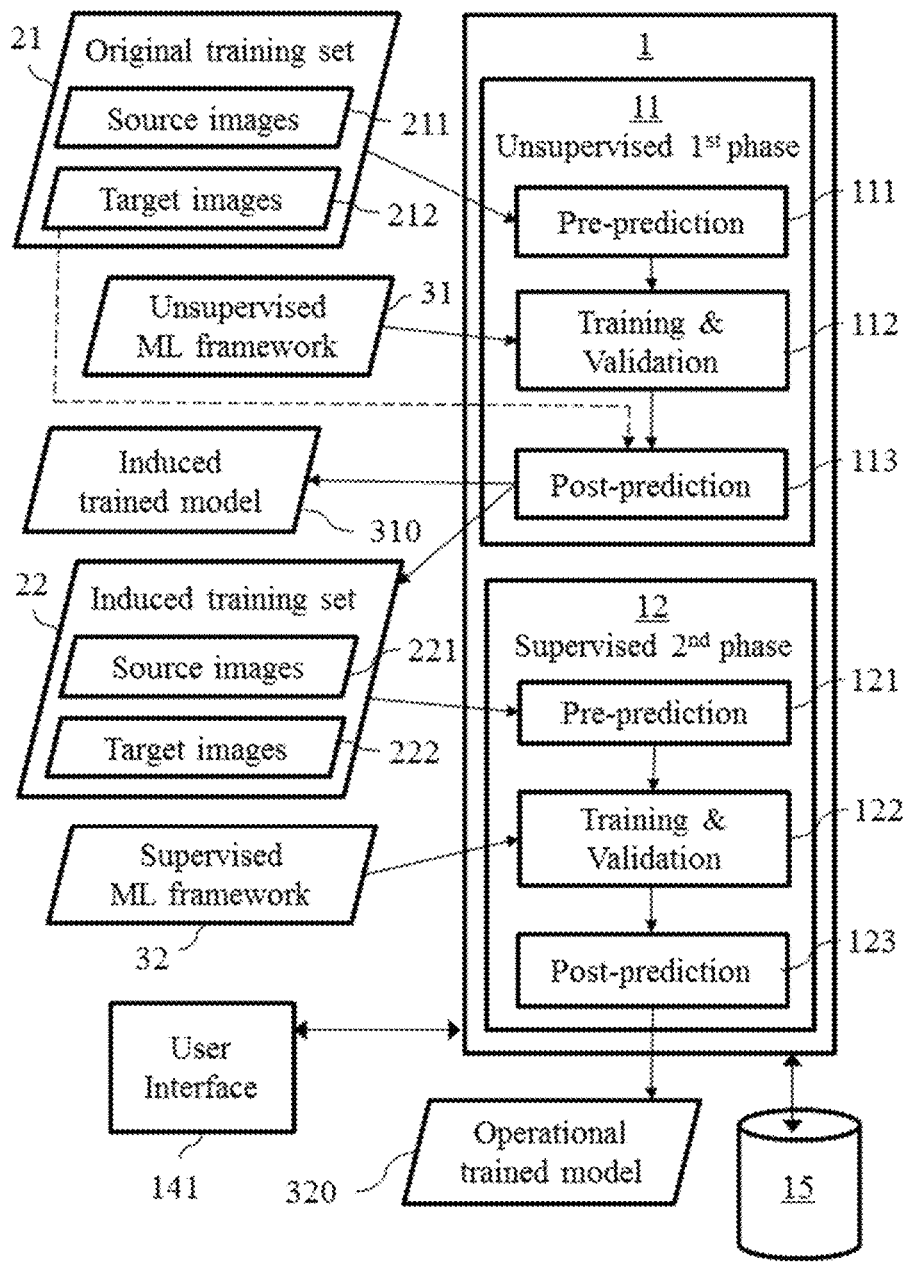
FIG. 1 is a block diagram representing schematically a device for synthesizing images compliant with the present disclosure.
Figure 2:
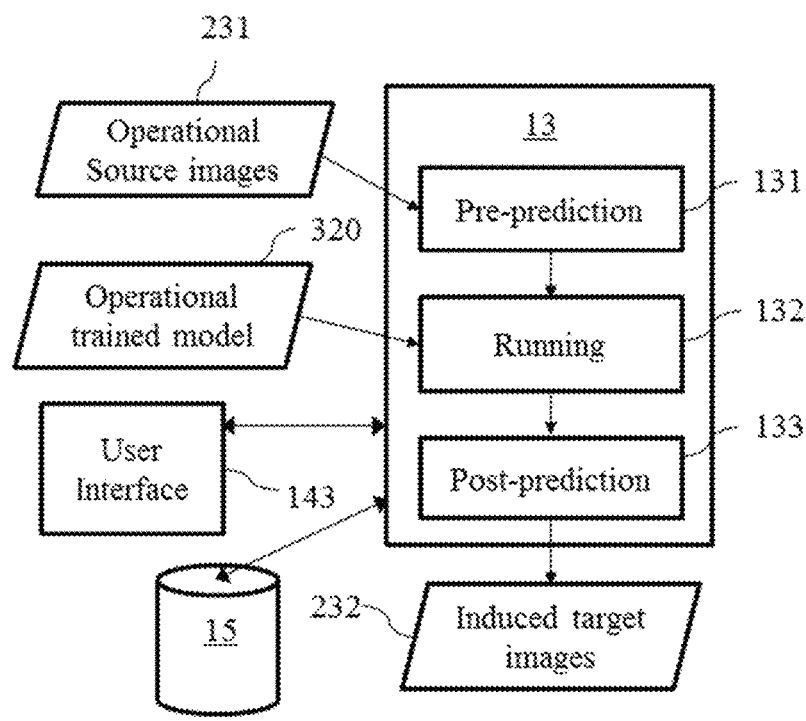
FIG. 2 is a block diagram representing schematically a production device associated with the device for synthesizing images of FIG. 1.

The present disclosure will be developed in reference to a particular functional embodiment of a device 1 for synthesizing images, as illustrated on FIG. 1, configured for producing by an ML process an operational trained model 320, from an original training set 21 of original source images 211 and of original target images 212. The disclosure will also be developed in reference to an associated production device 13, configured for integrating the trained model 320 provided by the device 1 so as to produce in running mode, synthetic operational target images 232 from input operational source images 231, as illustrated on FIG. 2.

Though the presently described devices 1 and 13 are versatile and provided with several functions that can be carried out alternatively or in any cumulative way, other implementations within the scope of the present disclosure include devices having only parts of the present functionalities.

Each of the devices 1 and 13 is advantageously an apparatus, or a physical part of an apparatus, designed, configured and/or adapted for performing the mentioned functions and produce the mentioned effects or results. In alternative implementations, any of the device 1 and the device 13 is embodied as a set of apparatus or physical parts of apparatus, whether grouped in a same machine or in different, possibly remote, machines. The device 1 and/or the device 13 may e.g. have functions distributed over a cloud infrastructure and be available to users as a cloud-based service, or have remote functions accessible through an API.

Also, the device 1 for synthesizing images and the production device 13 may be integrated in a same apparatus or set of apparatus adapted to carry out upstream ML and downstream production operations, and possibly intended to same users such as e.g. in the medical field, hospitals, health clinics, medical laboratories or radiologists. In other implementations, the structure of device 1 may be completely independent of the structure of device 13, and may be provided for other users. For example, the device 1 may be exploited by a dedicated operator proposing proper ML model construction to entities provided with running capabilities embodied in the device 13, either based on instances of the training set 21 independently available to the operator (e.g. from an online database or from directly collected relevant image sets), or based on instances provided by the client entities for this purpose. Alternatively, such an operator may be provided with the functionalities of both devices 1 and 13, so as to execute the ML and production actions on behalf of the client entities, by receiving instances of the operational source images 231 and by transmitting the induced synthetic target images 232 or further derived information, e.g. as subscribeware services (a.k.a. SaaS, for Software as a Service).

The original source images 211 and the operational source images 231 belong to a source domain while the original target images 212 and the synthetic target images 232 belong to a target domain. Those source and target domains are relevant to any appropriate image translation, typically in computer vision, image processing or computer graphics, e.g. image colorization, image segmentation, increase in resolution (notably super-resolution) or in dynamic range, style transfer, data augmentation, domain adaptation, contour detection, handwriting recognition, 3D reconstruction, or image translation from an imaging modality to another in the medical field.

In addition, the original source images 211 and target images 212 may be in the form of source-target pairs, each of them comprising possibly unaligned images (thus "unpaired"), or may instead include dissociated sets of the original source images 211 and of the target images 212. A mixture of both may also be used. Accordingly, the device 1 for synthesizing images is configured for executing an overall unsupervised learning in yielding the trained model 320 from the original training set 21.

The original training set 21 may be obtained in various ways, and possibly be derived from proprietary data and/or retrieved from remotely available public or private databases, for example from one or more local or remote database(s) 15. The latter can take the form of storage resources available from any kind of appropriate storage means, which can be notably a RAM or an EEPROM (Electrically-Erasable Programmable Read-Only Memory) such as a Flash memory, possibly within an SSD (Solid-State Disk). In variant implementations, the original training set 21 may be streamed to the device 1.

The devices 1 and 13 are interacting with respective user interfaces 141 and 143, via which information can be entered and retrieved by a user. Those user interfaces 141 and 143 include any means appropriate for entering or retrieving data, information or instructions, notably visual, tactile and/or audio capacities that can encompass any or several of the following means as well known by a person skilled in the art: a screen, a keyboard, a trackball, a touchpad, a touchscreen, a loudspeaker, a voice recognition system. The user interfaces 141 and 143 may be fused when the devices 1 and 13 are embodied in a same apparatus.

More will now be disclosed about the functionalities of the devices 1 and 13. The device 1 for synthesizing images in an unsupervised way has a two-stage nature, and includes an upstream first phase unit 11 and a downstream second phase unit 12. The first phase unit 11 is configured for carrying out an unsupervised learning and to produce an intermediate trained model 310 as well as an induced training set 22 of source images 221 and target images 222. The latter are organized in pairs, in which the source images 221 correspond to at least some and possibly all of the original source images 211, called kept source images, and the target images 222 correspond to the induced target images respectively obtained from the kept source images 221 through the unsupervised learning operations of the first phase unit 11. In this respect, the source-target images of each of those pairs in the induced training set 22 can be considered as (at least partly) aligned.

The second phase unit 12 is configured for carrying out an at least partly supervised learning on the ground of the induced training set 22, so as to produce the operational trained model 320. This unit 12 may however involve unsupervised components, insofar as it relies on the induced training set 22 through supervised steps in generating the trained model 320. The induced training set 22 may further be possibly completed with other aligned pairs of source and target images, obtained independently of the first phase unit 11. These may be obtained locally and/or remotely, for example from one or more of the local or remote database(s) 15.

The first phase unit 11 includes a pre-prediction module 111 adapted to prepare the original training set 21 before effective training steps. As visible on FIG. 3, it may notably be configured for implementing:

image preprocessing, possibly including noise removal or mitigation (submodule 161), registration to proper coordinate space(s) (submodule 162), clipping and/or scaling (submodule 163), and/or break-up (submodule 164) over image subspaces, such as e.g. channel color spaces for multi-channel images or directional views for multi-dimensional images (which may be axial, sagittal and coronal views for 3D medical images), and/or over reference image spaces such as e.g. atlases (which may be body atlases for 3D medical images).

Figure 4:
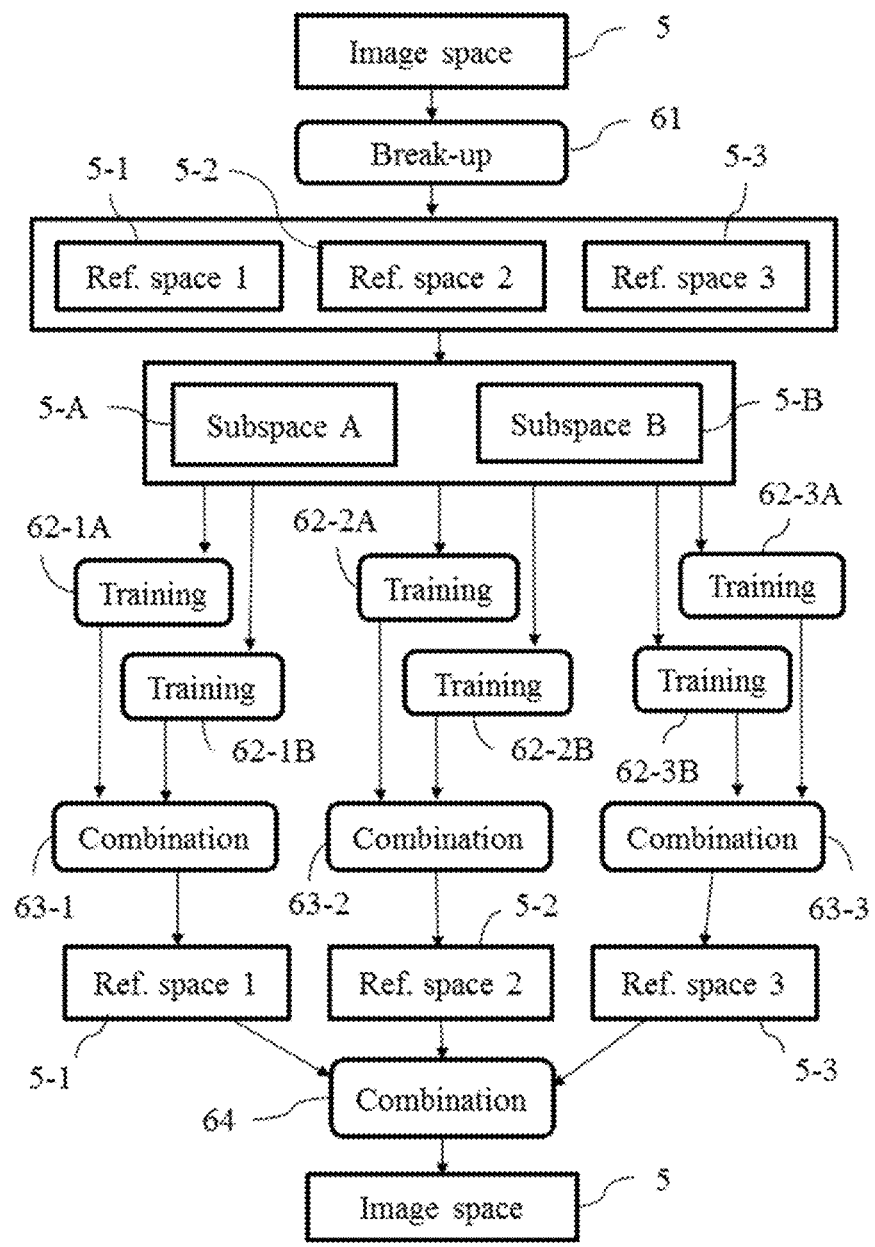
FIG. 4 provides a developed view of an exemplified break-up of a considered image space into multiple reference images spaces and subspaces, associated with training and ensembling operations, as carried out in a first phase with the device for synthesizing images of FIG. 1.

As exemplified on FIG. 4, a break-up 61 executed by the submodule 164 over an image space 5 may involve a distribution over reference image spaces 5-1, 5-2, 5-3 and image subspaces 5-A, 5-B. In downstream operations of the first phase unit 11, this is followed by dedicated training operations 62-1A, 62-1B, 62-2A, 62-2B, 63-3A, 63-3B over respective combinations of the reference image spaces and image subspaces, resulting in multiple respective elementary learning models and elementary (source and target) images, then subject to sub-combinations 63-1, 63-2, 63-3 with respect to the image subspaces and leading back to the reference image spaces 5-1, 5-2, 5-3, and to a further combination 64 leading back to the image space 5.

Though mentioned in the above order, the submodules 161, 162, 163 and 164 may in fact be arranged in any other way or possibly fused (e.g. image break-up by registering to reference image spaces), as relevant to the preparation of needed material.

The first phase unit 11 includes next in the processing stream an unsupervised training module 112, adapted to carry out the ML learning operations on the prepared material formed from the original training set 21 by the module 111 so as to produce raw material relevant to the induced training set 22 and to the trained model 310, by means of a first ML architecture associated with a first learning pipeline, jointly designated as a first ML framework 31 and providing an unsupervised process. The first ML framework 31 may notably be user-entered or retrieved from a local or remote database, such as the local or remote database(s) 15.

The training operations executed by the training module 112 may cover validation steps, enabling to derive proper hyper-parameters relevant to the trained model 310 (e.g. based on an original validation set including source and target images extracted from the original training set 21).

The unsupervised learning may involve deep generative models, such as GAN or VAE. The first ML framework 31 may be bidirectional. It may notably comprise a GAN model ensuring cycle consistency, and be compliant with any of above-cited CycleGAN, DiscoGAN, DualGAN or HarmonicGAN. It may instead rely on a shared latent space and implement any of above-cited UNIT, CoGAN or MUNIT.

Figure 5A:
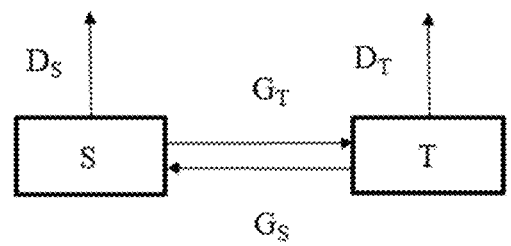
FIGS. 5A, 5B and 5C schematically illustrate aspects of an ML training process suited to a first phase unit of the device of FIG. 1, involving a generative adversarial architecture and cycle consistency, by showing the generative-discriminative approach (5A), the forward-backward consistency (5B) and the backward-forward consistency (f5C)
Figure 5B:
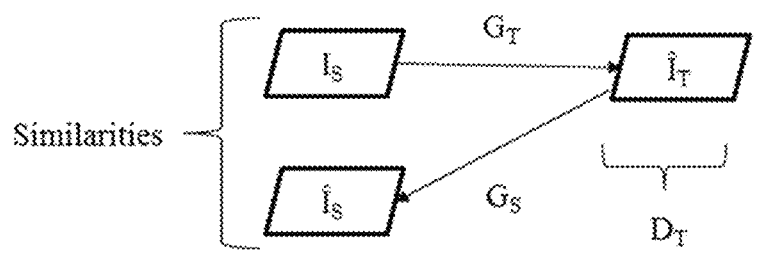
Figure 5C:
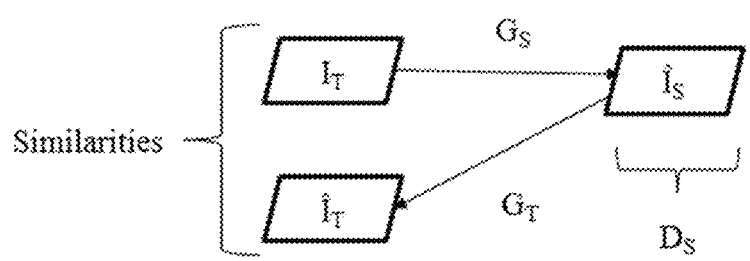

In particular, the combination of GAN and cycle consistency may be modeled as involving two generative mapping functions between a source space S and a target space T, as illustrated on FIG. 5A: one $G_T$ from space S to space T suited to generate target items from source items, and one $G_S$ from space T to space S suited to generate source items from target items. It also relies on two adversarial discriminators $D_T$ and $D_S$, respectively adapted to penalize generator attempts to produce synthetic candidates indistinguishable in the target and source domains. This may be expressed in the learning pipeline through adversarial losses in an objective, as known to a skilled person. The forward cycle consistency is enforced (FIG. 5B), when transforming a source image sample $I_S$ of the source domain to a synthetic target image sample $\hat{I}_T$ in the target domain and then the latter back to a synthetic source image sample is in the source domain, by ensuring similarity between the original source image sample $\hat{I}_S$ and the synthetic source image sample $\hat{I}_S$. This may be performed e.g. using simple image similarity metrics such as L1 or L2 distances. Likewise (FIG. 5C), the backward cycle consistency is enforced, when transforming a target image sample $\hat{I}_T$ of the target domain to a synthetic source image sample $\hat{I}_S$ in the source domain and then the latter back to a synthetic target image sample $\hat{I}_T$ in the target domain, by ensuring similarity between the target source image sample $\hat{I}_T$ and the synthetic target image sample $\hat{I}_T$. Both together provide the cycle consistency, which may be obtained by proper similarity terms (cycle consistency losses) in the objective.

In addition, convolutional layers may be exploited in the first ML framework 31 in CNNs or F-CNNs, from the source domain to the target domain, and in the reverse direction in case the ML architecture is bidirectional. The F-CNNs may take the form of, or be similar to, a U-Net.

Multiple distinct models may be trained, e.g. in parallel, corresponding to the respective image subspaces and reference image spaces considered in the break-up executed in submodule 164 (see FIG. 4).

Figure 6:
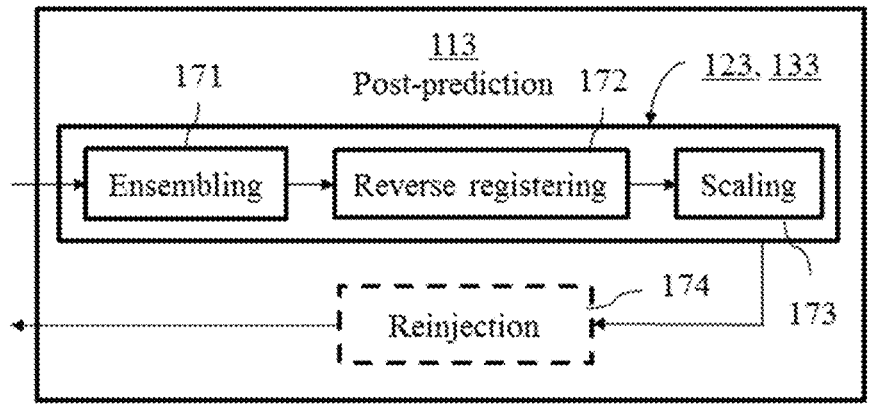
FIG. 6 focuses on a post-prediction module exploited in particular embodiments of the device for synthesizing images of FIG. 1 and of the associated production device of FIG. 2, in relation with the pre-prediction module of FIG. 3.

The first phase unit 11 further includes a post-prediction module 113, adapted to receive the raw material from the module 112 and to generate from it the induced training set 22 and optionally the intermediate trained model 310. As visible on FIG. 6, the post-prediction module 113 may notably be configured for implementing:
  ensembling (submodule 171), possibly mirroring the break-up operations of submodule 164 by combining the results from the respective models so as to reconstruct a global space,
  reverse registering (submodule 172), possibly mirroring the registration effected by submodule 162 (e.g. by inverse warping from a working grid to an original grid) so as to return to the original space of the source and/or the target domain (see FIG. 4),
  scaling (submodule 173), possibly mirroring the scaling executed by submodule 163 so as to reposition the results within an expected range, and/or
  reinjection of particularities of the original target images 212 (submodule 174) into target instances of the induced training set 22.

Though mentioned in the above order, the submodules 171, 172, 173 and 174 may in fact be arranged in any other way or possibly fused (e.g. image reconstruction by inverse registering from reference image spaces to an original image space in an ensembling process), as relevant to the generation of the induced training set 22.

The optional operations of submodule 174 may at first sight look redundant, insofar as the induced target images obtained through the unsupervised learning process of the training module 112 already incorporates features of the original target images 212 and furthermore, are based thereon. However, proceeding with such a reinjection may significantly enhance the relevance of those images, and hence the quality performance of the following steps operated by the second phase unit 12.

The induced target images may be transformed, enhanced or supplemented in various ways so as to produce the target images 222 of the induced training set 22. For example, contours, features, colors, resolution or dynamic range may be enhanced by cross-correlations or combinations between the original and the corresponding induced target images obtained through the unsupervised learning process of the training module 112.

In particular implementations, the original training set 21 includes one or more unaligned ("unpaired") but corresponding image pairs, e.g. in medical imaging being obtained for a same organ of a same patient, though via two distinct imaging modalities. Then, for any of those pairs, the submodule 174 may be configured for independently executing reinjection operations from the original target images 212 into the expressly corresponding induced target images.

In other implementations, the submodule 174 is configured for generating the target images 222 of the induced training set 22 by aligning (i.e. registering) the original target images 212 to the corresponding induced target images. Namely, in such implementations, the induced target images are not merely transformed, enhanced or supplemented in generating the induced training set 22: in fact, they are not even kept for the following second phase once they have been exploited. By contrast, the use of the original target images 212 is pursued through their deformed versions into the induced training set 22. The role of the induced target images is thus directed to providing appropriate topological transformations to the original target images 212 for gaining alignment with the original source images 211. This may provide a particularly high-quality account of the original training set 21 in the aligned image pairs of the induced training set 22, not only in the source images 221 that can be directly derived from the original source images 211, but also in the target images 222. Indeed, the whole content of the original target images 212 may then be expressly preserved.

An alignment of the original target images 212 to the induced target images may e.g. be performed by using a deformable registration algorithm as disclosed by B. Glocker et al. in "Deformable medical image registration: setting the state of the art with discrete methods", Annual Review of Biomedical Engineering, 13(1), pp. 219-244, 2011.

In this way, the original source images 211 and target images 212 of the original training set 21 may be eventually aligned without having to do a cross-alignment directly between them, but via the induced target images. The alignment can thereby be much better, keeping in mind that alignment between source and target images, notably cross-modality registration in medical imaging, is usually not trivial and can sometimes be very challenging. Indeed, simpler objectives can be used in aligning the original target images 212 and the induced target images, like sum of absolute differences for alignment optimization, which would not be possible through direct alignment between the original source images 211 and target images 212.

In some embodiments, the submodule 174 is adapted to combine two or more implementations. For example, only part of the original training set 21 is made up of image pairs, so that the reinjection process is either executed only for the image pairs, or takes on distinct forms for the image pairs and the other images. In another example, some of the image pairs comprise sufficiently corresponding source and target images, even though unaligned, while other image pairs comprise more disparate images (e.g. in medical imaging, same organs of quite dissimilar patients). Then again, the reinjection process may be conditionally carried out or take on different forms, depending on similarity criteria between the source and target images of the pairs.

As will be apparent to the reader below, the intermediate trained model 310 may be useless in the following steps, and consequently ignored. In variants, the trained model 310 may instead be exploited for generating additional aligned image pairs relevant to the supervised learning of the second phase unit 12, based on available original further source images, possibly associated for part or all of them with respective further target images.

Figure 3:
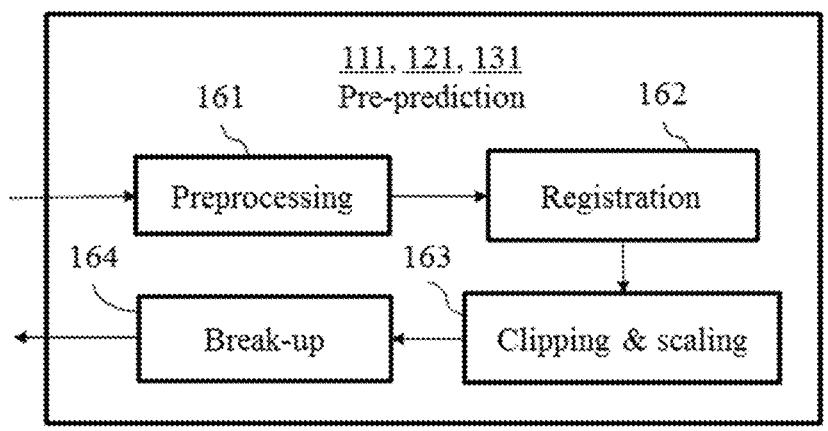
FIG. 3 focuses on a pre-prediction module (the prediction referring to training or production running operations) exploited in particular embodiments of the device for synthesizing images of FIG. 1 and of the associated production device of FIG. 2.

The second phase unit 12 includes a pre-prediction module 121 adapted to prepare the induced training set 22 before effective training steps. It may include functionalities similar to those of the pre-prediction module 112 of the first phase unit 11, so that the reader is referred to the above related description (FIG. 3).

However, in the break-up submodule 164, less image subspaces and possibly less image reference spaces may be possibly dealt with in the second phase unit 12 compared with the first phase unit 11. Indeed, due to the supervised nature of the following learning process, a same level of quality may be obtained based on a smaller number of those image subspaces or image reference spaces.

Figure 7:
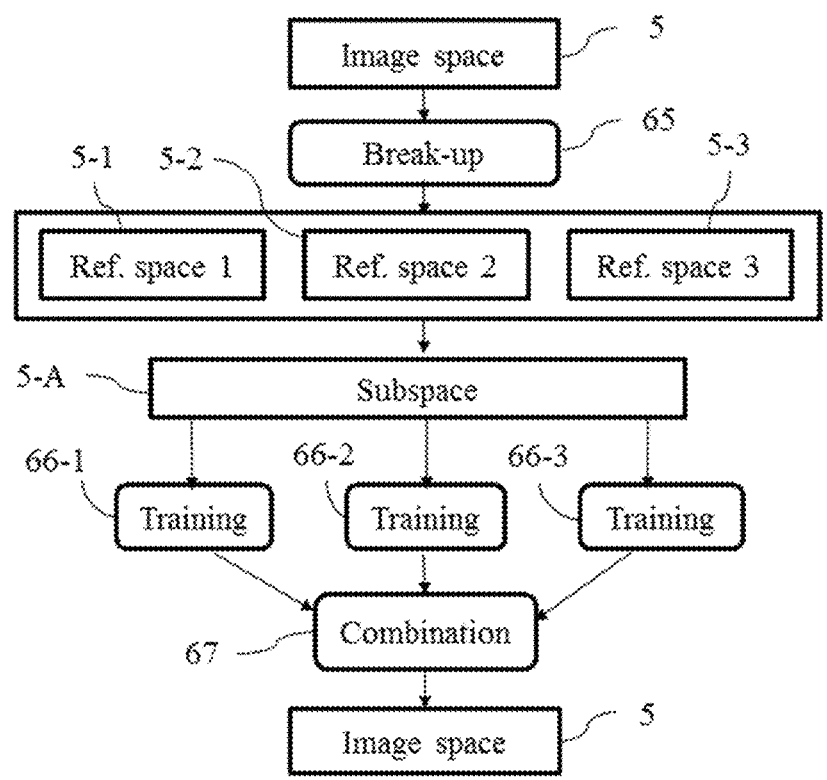
FIG. 7 provides a developed view of an exemplified break-up of a considered image space into multiple reference images spaces and subspaces corresponding to the break-up of FIG. 4, associated with training and ensembling operations, as carried out in a second phase with the device for synthesizing images of FIG. 1 as well as with the production device of FIG. 2.

As exemplified on FIG. 7 in relation with the above break-up applied in the first phase unit 11 (FIG. 4), a break-up 65 executed by the submodule 164 over an image space 5 may involve a distribution over reference image spaces 5-1, 5-2, 5-3 like for the unsupervised training of the first phase, but over only image subspace 5-A and no longer 5-B. In downstream operations of the second phase unit 12, this is followed by dedicated training operations 66-1A, 66-2A, 66-3A over combinations of the reference image spaces and the considered image subspace, resulting in multiple respective elementary learning models and elementary (source and target) images, then subject to combination 67 leading back to the image space 5.

The second phase unit 12 includes next in the processing stream an (at least partly) supervised training module 122, adapted to carry out the ML learning operations on the prepared material formed from the induced training set 22 by the module 121 so as to produce raw material relevant to the trained model 320, by means of a second ML architecture associated with a second learning pipeline, jointly designated as a second ML framework 32. That second ML framework 32 may notably be user-entered or retrieved from a local or remote database, such as the local or remote database(s) 15.

The training operations executed by the training module 122 may cover validation steps, enabling to derive proper hyper-parameters relevant to the trained model 320 (e.g. based on an induced validation set including source and target images extracted from the induced training set 22).

The supervised learning may be executed in any manner known to a skilled person, e.g. relying on CNNs. Anyway, in advantageous implementations, it is combined with an unsupervised learning component—which may reflect in a proper architecture and in a loss function combining supervised and unsupervised learning terms.

In particular implementations directed to mixed supervised-unsupervised learning, the second ML framework 32 involves a generative model, such as GAN or VAE. For example, the second ML framework 32 includes an architecture compliant with a conditional GAN (cGAN) and a pipeline possibly compliant with pix2pix, as referred to above.

In addition, convolutional layers may be exploited in the second ML framework 32 in CNNs or F-CNNs. The F-CNNs may take the form of, or be similar to, a U-Net.

Cycle consistency may be enforced, too, the second ML framework 32 being then e.g. compliant with any of above-cited CycleGAN, DiscoGAN, DualGAN or HarmonicGAN.

It may instead rely on a shared latent space and implement any of above-cited UNIT, CoGAN or MUNIT. It deserves noting that with cycle consistency and resultant bidirectional processing, the supervision based on the induced training set 22, which is normally executed at the target image side, may further be executed also at the source image side. This may be introduced in the learning pipeline through proper corresponding similarity terms in the loss function.

Figure 8A:
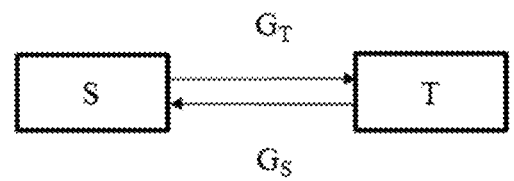
FIGS. 8A, 8B and 8C schematically illustrate aspects of an ML training process suited to a second phase unit of the device of FIG. 1, involving a generative adversarial architecture together with a supervised learning pipeline, by showing the generative-discriminative approach (8A), the forward similarity enforcement (8B) and the backward similarity enforcement (8C)
Figure 8B:
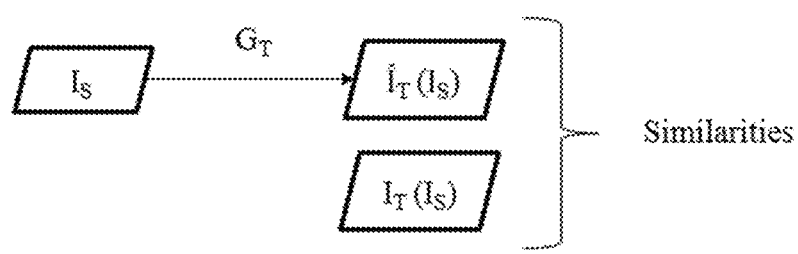
Figure 8C:
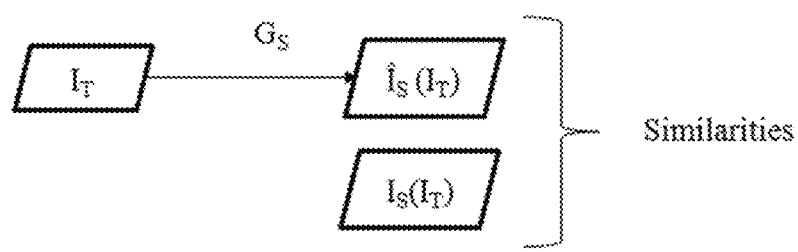

A combined supervised and generative adversarial learning implemented by the training module 122 may be modeled as involving two generative mapping functions between a source space S and a target space T, in the same way as the example generative model implemented by the training module 112 and as illustrated on FIG. 8A. However, it further includes (FIG. 8B) forward similarity enforcement between a synthetic target image sample $\hat{I}_T (I_S)$ obtained from a source image sample $I_S$ with the generator $G_T$ on one hand, and a target image sample $I_T$ paired with the source image sample $I_S$ in the considered training set (the induced training set 22) on the other hand. Likewise, with regard to the bidirectional property, it also includes (FIG. 8C) backward similarity enforcement between a synthetic source image sample $\hat{I}_S (I_T)$ obtained from a target image sample $I_T$ with the generator $G_S$ on one hand, and a source image sample $I_S$ paired with the target image sample $I_T$ in the considered training set on the other hand. Both together provide a supervised similarity based on the training set 22, which may be obtained by proper similarity terms in the objective (e.g. L1 or L2 losses, possibly completed by local normalized cross correlation).

With respect to the first ML framework 31, the second ML framework 32 may be alleviated, namely be made less computationally demanding. This may be obtained e.g. by using a substantially smaller number of weights and biases, or of filters in CNNs or F-CNNs (a filter amounting to a set of weights and biases) and/or by exploiting a reduced number or ANN layers.

In particular implementations, the ML architecture of the second ML framework 32 is similar to the ML architecture of the first ML framework 31, subject to a reduction in the numbers of weights and biases and/or of ANN layers. In a more specific embodiment, those ML architectures include CNNs or F-CNNs having the same numbers of layers, but the numbers of weights and biases, or the numbers of filters, are decreased with a same proportionality factor for all or part of those layers.

Insofar as the second ML framework 32 is lighter than the first ML framework 31, this can reflect in the production pipeline exploited downstream in production operations. Consequently, the running of the operational trained model 320 may be substantially more computationally efficient than the trained model 310, while potentially preserving a similar quality level.

Admittedly, with respect to a one-stage unsupervised learning process as known in the art, the present second phase requires additional computation operations which cumulate with those of the first phase. However, once done, this may result in substantially more efficient operational running In particular, real-time image translation may become possible where previously jeopardized by resource limitations.

Also, supervised learning algorithms are known to yield better performance than their unsupervised counterparts, due to the simple fact that the problem gets a lot simplified with the presence of reference labels, as navigation through a plausible solution space is guided by more well defined and constrained objectives. Where the reference labels are ground truth labels, as possibly obtained with the reinjection submodule 174, the quality of the results may be all the better.

Multiple distinct models may be trained, e.g. in parallel, corresponding to the respective image subspaces and reference image spaces considered in the break-up executed in the pre-prediction module 121.

The second phase unit 12 further includes a post-prediction module 123, adapted to receive the raw material from the training module 122 and to generate from it the operational trained model 320. It may include functionalities similar to those of the post-prediction module 113 of the first phase unit 11 except for the reinjection submodule 174 (which makes sense only for the first phase unit 11), so that the reader is referred to the above related description (FIG. 6)—the mentioned mirroring referring to the operations executed by the pre-prediction module 121.

The production device 13 (FIG. 2) is configured for receiving or retrieving the operational trained model 320, which may be directly obtained from the device 1 or possibly retrieved from proprietary data and/or from remotely available public or private databases, for example such as the local or remote database(s) 15.

It includes a pre-prediction module 131 adapted to prepare the operational source images 231, which may include functionalities similar to those of the pre-prediction module 121 of the second phase unit 12, the break-up submodule 164 included, so that the reader is referred to the above related description (FIG. 3).

It further includes a running module 132, configured for applying the operational trained model 320 to the operational source images 231 once prepared by the pre-prediction module 131.

This is followed by a downstream post-prediction module 133 similar to the post-prediction module 123 of the second phase unit 12 (FIG. 6), and adapted to process the material relevant to the synthetic target images and generated by the operational trained model 320 so as to produce the induced synthetic target images 232.

The transmissions between the devices 1 and 13 on one hand and the database(s) on the other hand, and between the devices 1 and 13 when not integrated in a same apparatus, may be effected via any appropriate communication network involving wired (e.g. Ethernet), wireless (e.g. WiFi, WiMax—standing for Worldwide interoperability for Microwave Access, or Bluetooth) or cellular (e.g. UMTS—standing for Universal Mobile Telecommunications System, LTE—standing for Long-Term Evolution, or 5G) transmissions, as well known to a person skilled in the field.

Figure 9:
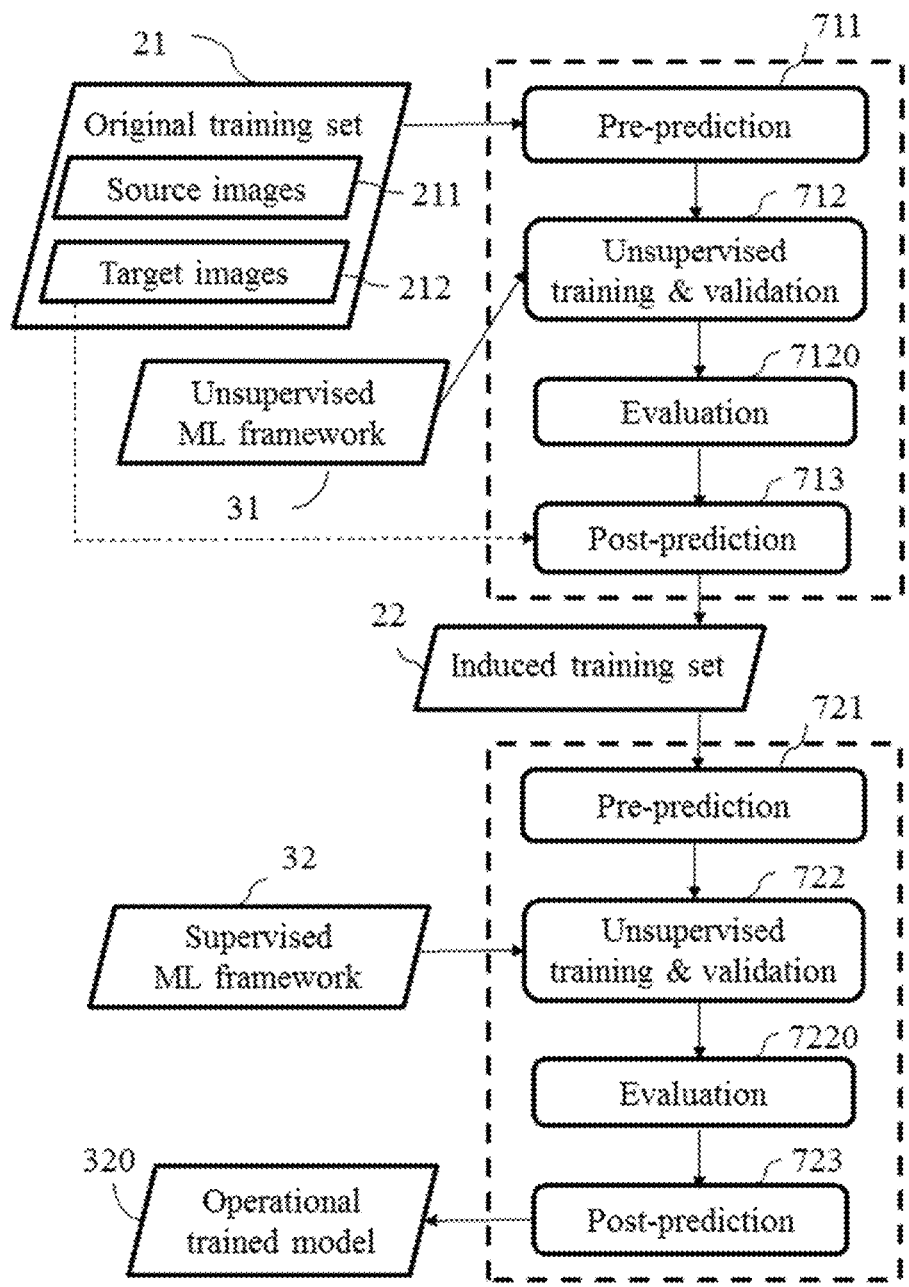
FIG. 9 is a flow chart showing successive steps executed with the device for synthesizing images of FIG. 1.

In operation, the device 1 may for example execute the following process, in relation with FIG. 9:
- receive the original training set 21 and apply preliminary preparation operations (step 711), possibly including preprocessing, registration, clipping and scaling, and/or break-up, as explained above;
- apply to the original training set 21 after preparation the unsupervised learning (training and validation) defined by the first ML framework 31, so as to generate material relevant to a set of paired images (step 712);
- possibly proceed with an evaluation of the results with a test dataset (step 7120), e.g. removed from the original training set 21 (so that an effective training set, a validation set and a test set may be originally provided);
- post-process the obtained material to produce the induced training set 22 of paired images (step 713), possibly including ensembling, reverse registering, scaling and/or reinjection as explained above;
- apply preliminary preparation operations to the induced training set 22 (step 721), possibly including preprocessing, registration, clipping and scaling, and/or break-up, as explained above;
- apply to the induced training set 22 after preparation the (at least partly) supervised learning (training and validation) defined by the second ML framework 32, so as to generate material relevant to an operational trained model (step 722);
- possibly proceed with an evaluation of the results with a test dataset (step 7220), e.g. removed from the induced training set 22 (so that an effective training set, a validation set and a test set may be then provided);
- post-process the obtained material to obtain and produce the operational trained model 320 (step 723), possibly including ensembling, reverse registering and/or scaling as explained above.

Figure 10:
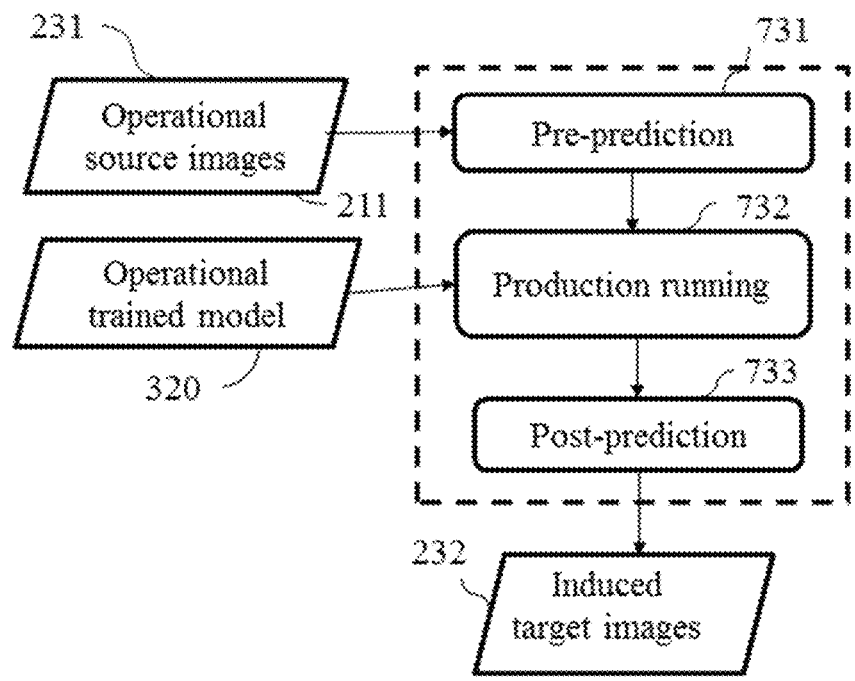
FIG. 10 is a flow chart showing successive steps executed with the production device of FIG. 2.

In operation, the device 13 may for example execute the following process once the operational trained model 320 is loaded, in relation with FIG. 10:
- receive the operational source images 231 and apply preliminary preparation operations (step 731), possibly including preprocessing, registration, clipping and scaling, and/or break-up, as explained above;
- run the prepared operational source images 231 with the operational trained model 320 so as to generate material relevant to induced synthetic target images (step 732);
- post-process the obtained material to obtain and produce the induced synthetic target images 232 (step 733), possibly including ensembling, reverse registering and/or scaling as explained above.

Applications to Treatment Planning

Figure 11:
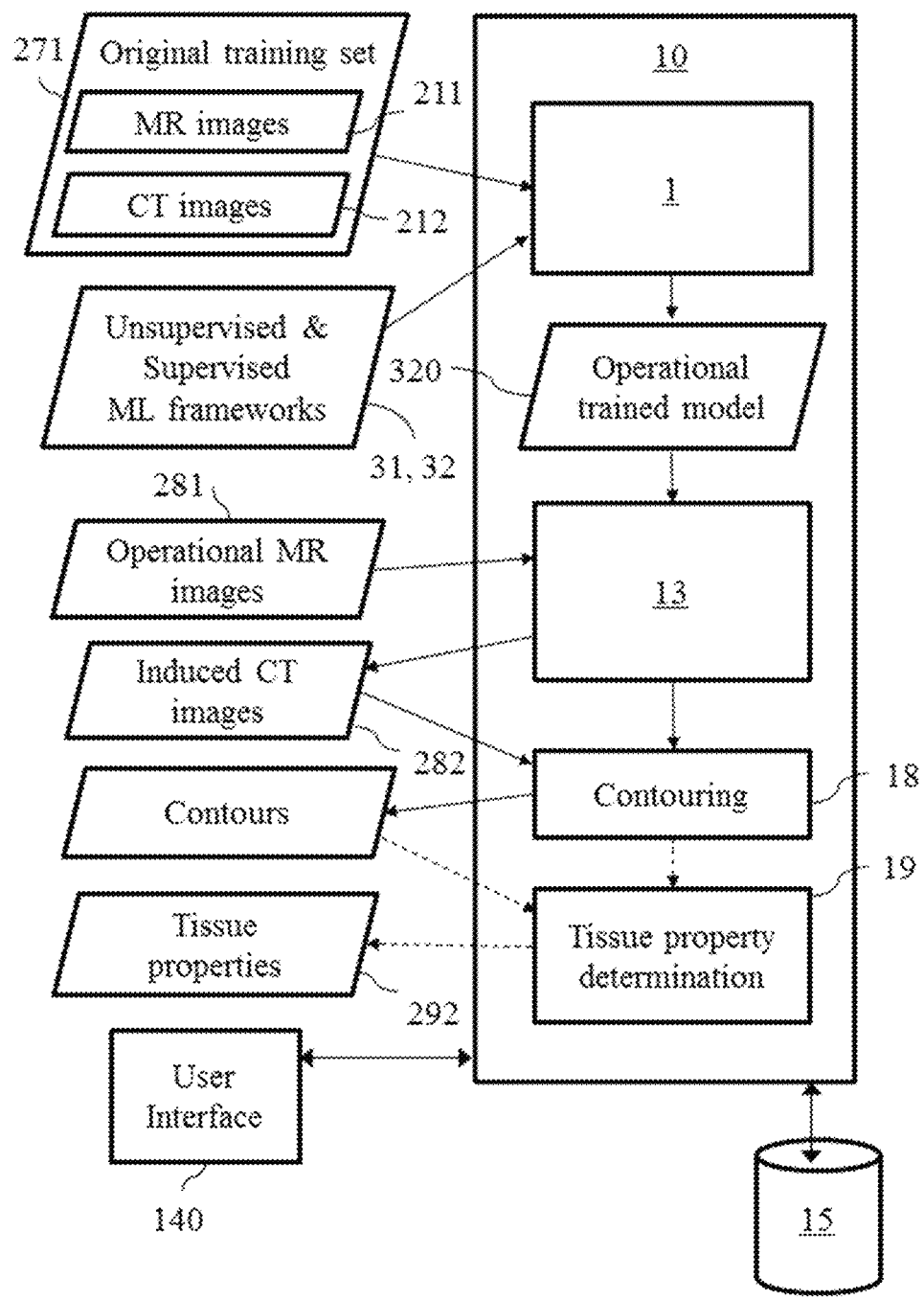
FIG. 11 is a block diagram representing schematically a device for treatment planning, comprising notably the device for synthesizing images of FIG. 1 applied to the translation of MR images to CT images, adapted to provide organ tissue properties with a view to radiation dose delivery.

Applications of the disclosure in the medical field will now be specifically described, regarding more precisely the translation of unpaired MR images to CT images. In this respect, as represented on FIG. 11, a device 10 for treatment planning includes the device 1 for synthesizing images and the production device 13. The device 10 is cooperating with a user interface 140 similar to the above-described user interfaces 141 and 143, and is configured for receiving an original training set 271 of MR and CT images, respectively as source and target images, so as to generate an operational learning model as previously disclosed about the device 1. It is also configured for receiving operational MR images 281 in production working, and to translate those MR images 281 to induced synthetic CT images 282, as previously disclosed about the device 13.

In addition, the device 10 for treatment planning includes a contouring module 18, adapted to receive the induced synthetic CT images 282 and to automatically contouring organs on the latter, so as to produce contour information 291. This may be helpful in segmenting out organs at risk on the synthetic CT images 282. The contouring module 18 may notably be previously trained on original CT scans.

Optionally, the device 10 comprises downstream a module 19 for tissue property determination, configured for automatically determining organ tissue properties 292 from the induced synthetic CT images 282 and the contour information 291, and for outputting them to a user with a view to simulating the impact of radiation dose delivery.

Detailed examples below of the device 10 for treatment planning will enable the reader to enter more in-depth into effective implementations compliant with the disclosure. As a matter of fact, getting good quality paired training data for supervised learning is always a challenge, paired data being created by aligning the ground truth CT volume to the input MRI volume. This cross-modality alignment process is not trivial and can be very challenging for anatomies that change shape considerably over time. The bladder and the intestines in the pelvic region for instance vary a lot in shape and size with time, and even for CT and MRI taken in a close time frame, they could change significantly. The limitations of cross-modality image registration therefore make it difficult to obtain high quality paired data for supervised learning.

The present device 1 for synthesizing images, and its encompassing device 10 for treatment planning, may retain the advantages of a completely supervised learning algorithm while significantly eliminating from the pipeline the alignment errors caused by medical image registration algorithm when dealing with cross-modality image registration. This may be achieved by the unsupervised data generation step as a prior that allows for better registration (the first phase unit 11), and thus in turn better quality ground truths for supervised learning (the second phase unit 12).

Also, subject to the embodiments involving the submodule 174 by using the induced CT outputs of the unsupervised first phase as a target for registration of the initial CT, adopted below, the original CT and MR images (original training set 21) can be eventually aligned without having to do a cross-modality image registration directly between them.

1/ First Phase Implementation (Unsupervised)

The first phase unit 11 (pre-prediction module 111) computes an external contour for the MR and CT images of the original training set 271, using an external contour generation algorithm as known to a skilled person, and removes everything lying outside a patient volume. The removal includes random noises in the MR images and the couch and other instruments in the CT scans. This is e.g. achieved by setting the voxel values outside the patient volume to 0 in MRI and to −1024 HU (standing for Hounsfield Units) in CT scans (−1024 corresponding to the value for air).

A rigid registration is then performed between the resulting CT and MR images, followed by an affine registration between the rigid registered CT images and full body atlas CTs, which generates an affine registration matrix. Such a full body atlas, which is a particular case of the abovementioned reference image spaces, comprises essentially high resolution (2 mm, 0.98 mm, 0.98 mm) CT scans of the entire body, used as reference to move all input data to a common space. Subsequently, the MR and registered CT images are moved to an atlas grid using that affine registration matrix. This results in having all volumes on the same image grid.

Four full body atlases are exploited in the above process of affine registration, thus generating four copies of each volume in four different grids. Each of those four copies differs from the others since the atlases vary in their anatomical features, thus creating slight differences in volumes.

The data generated on the four atlases are used to train in parallel four different models that are then combined towards the end to given the synthetic CTs (also called pseudo CTs). All following steps of the first phase are accordingly carried out on all the four copies of the volume simultaneously—unless stated otherwise.

Once the volumes are cleaned and moved to a common grid, the intensity range of the CT images is clipped within −1000 to 500 HU, while intensity range of the MR images is clipped at 99.8 percentile to account for the presence of any machine artifacts that might have been present on the image. Both CT and MRI volumes are then scaled between −1 and 1.

The image generation algorithm operates on 2D slices rather than 3D volumes. Hence, slices of each volume are taken in axial, sagittal and coronal views, which are particular cases of the above-mentioned image subspaces. Those slices are used for training multiple models in different views. Among the potential slices, not all of them are picked for training, but e.g. randomly one out of every 8 slices for each volume. Indeed, consecutive slices mostly have redundant information. This generates the proper dataset for training and validation.

Figure 12:
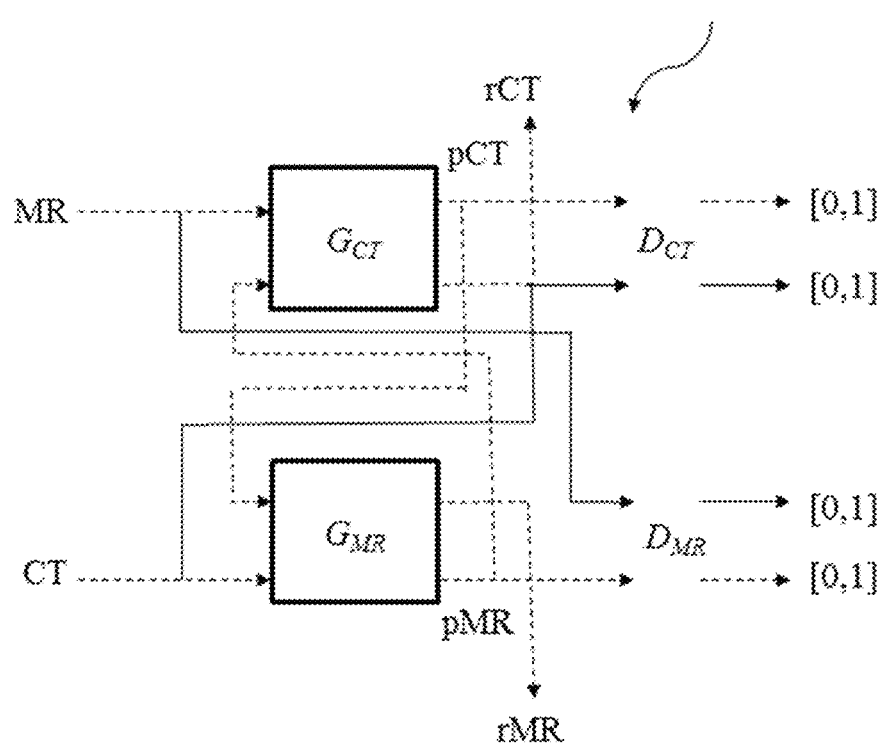
FIG. 12 shows a CycleGAN bidirectional pass workflow, exploited in first and second phases of the ML process implemented in the device of FIG. 11.

For the first ML framework 31 (training module 112), a CycleGAN training is used, thus allowing image generation from MRI to CT and conversely. As visible on FIG. 12, an exploited CycleGAN framework 35 includes four different neural network models comprising:

2 generator networks $G_{CT}$ (also noted $G_{MR \to CT}$) and $G_{MR}$ (also noted $G_{CT \to MR}$), one for generation of pseudo CT ("pCT") from MR images ($G_{CT}$), which are subject to post-prediction operations, and the other for generation of pseudo MR ("pMR") from CT images ($G_{MR}$);

2 discriminator networks $D_{CT}$ and $D_{MR}$, whose functions consist respectively in distinguishing real CT from generated CT ($D_{CT}$), and real MR from generated MR ($D_{MR}$).

The pseudo CT images are used to train the discriminator $D_{CT}$ against the original CT images, and to reconstruct original MR images via the generator $G_{MR}$ as reconstructed rMR images. Likewise, the pseudo MR images are used to train the discriminator $D_{MR}$ against the original MR images, and to reconstruct original CT images via the generator $G_{CT}$ as reconstructed rCT images. The reconstructed rMR and rCT images are then compared to the original MR and CT images, using image similarity losses.

The algorithm is further completely deterministic, insofar as once the models are trained, it always generates the same CT image for a given MR image, and vice versa. In this regard, it is ensured that the architectures do not use any test time dropouts or random noise seeds for image generation.

Figure 13:
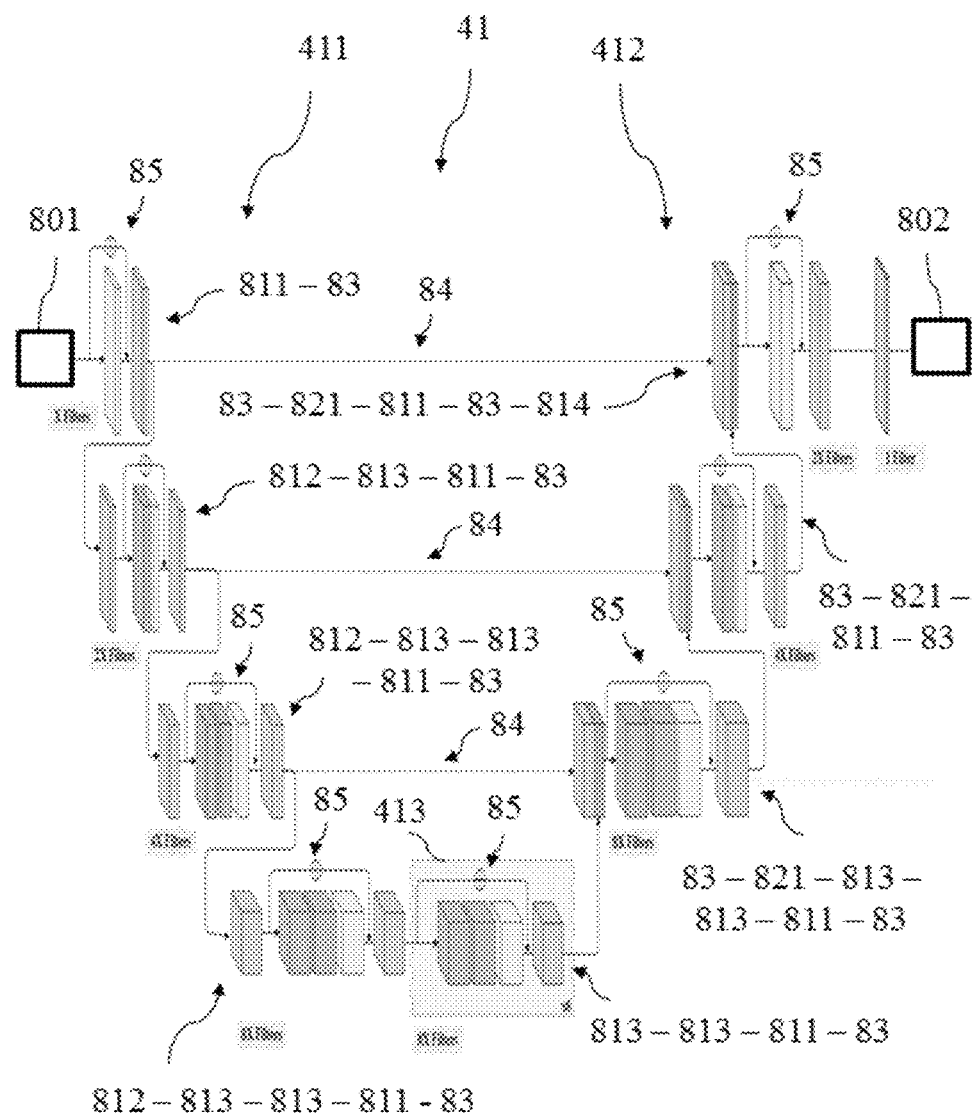
FIG. 13 details an example of an F-CNN architecture used in generators integrated in the CycleGAN bidirectional pass workflow of FIG. 12.

The generators $G_{CT}$ and $G_{MR}$ are for example compliant with an F-CNN generator 41 of a U-Net kind, as represented on FIG. 13, and comprises an encoder side 411 coupled with a decoder side 412 exactly symmetrical to the latter. The generator 41 is either adapted to receive MR slices 801 as inputs and to generate pCT slices 802 as outputs ($G_{CT}$), or to receive CT slices 801 as inputs and to generate pMR slices 802 as outputs ($G_{MR}$). For sake of conciseness, main aspects of the generator 41 are developed below, specially where specific with respect to known U-Net structures, and complementary information may be found about the background in particular in the above-cited article by O. Ronneberger et al. pertaining to U-Net architecture.

The generator 41 is built on multiple layers including:
convolution blocks 811 dedicated to 5×5 Conv2D (Stride 1)+InstanceNorm,
convolution blocks 812 on the encoder side 411, dedicated to 2×2 Conv2D (Stride 2)+InstanceNorm+ReLU,
convolution blocks 813 dedicated to 5×5 Conv2D (Stride 1)+InstanceNorm+ReLU,
transposed convolution blocks 821 on the decoder side 412, dedicated to 2×2 ConvTranspose2D (Stride 2)+InstanceNorm+ReLU, a convolution block 814 on the decoder side 412 and having a single filter, dedicated to 1×1 Conv2D (Stride 1)+Tanh, ReLU blocks 83, where:

"W×H Conv2D (Stride S)" and "W×H ConvTranspose2D (Stride S)" stand respectively for a 2D convolutional layer and a 2D transpose convolutional layer having a kernel of width W and height H, and a stride S, "InstanceNorm" designates an instance normalization, as described by D. Ulyanov, A. Vedaldi and V. Lempitsky in "Instance normalization: The missing ingredient for fast stylization", 2016, arXiv: 1607.08022.

Accordingly, all feature channels are instance normalized and have a ReLU activation, except for the final layer (block 814) which has a tanh activation.

On the encoder side 411, the first convolution block 811 has 64 filters (X=64), and the number of filters is then rising exponentially with each downsampling (passages to blocks 812). The downsampling operations on the feature maps are repeated three times, so that the lowest resolution of the feature maps is only $\frac{1}{8}^{th}$ of the original input resolution. Several residual blocks (transformation bridge 413 of successive blocks 813, 813, 811 and 83) are added at the lowest resolution before upsampling.

On the decoder side 412, the first transpose convolution is based on 512 filters, and the number of filters is exponentially decreased at each upsampling operation down to 128 filters just before the last convolution block 814. In addition, long range skip connections 84 are provided for concatenations between stages of the encoder side 411 and decoder side 412, as known for U-Net configurations.

Further, residual connections 85 are introduced at each downsampling and upsampling step, and in the transformation bridge 413.

Figure 14:
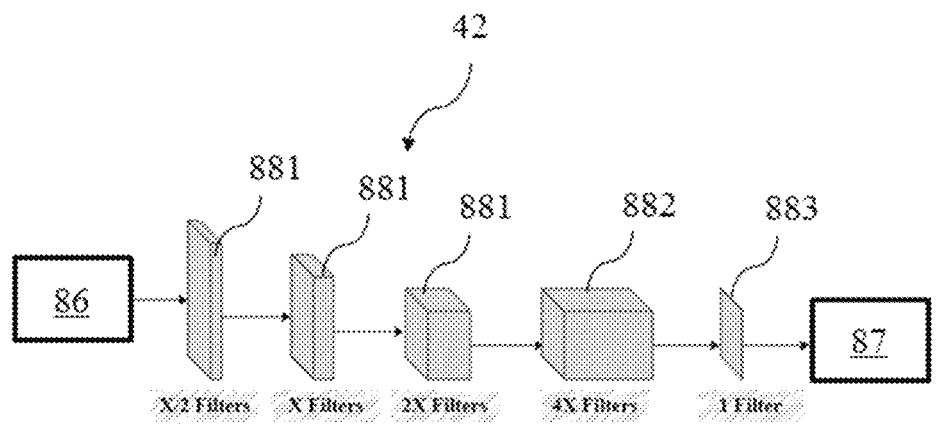
FIG. 14 details an example of an F-CNN architecture used in discriminators integrated in the CycleGAN bidirectional pass workflow of FIG. 12.

The discriminators $D_{CT}$ and $D_{MR}$ are for example compliant with a discriminator 42 having a convolutional architecture, as represented on FIG. 14, which penalizes structure at the scale of patches. Such a discriminator tries to classify if each N×N patch in an image is real of fake, averaging all responses across an image to provide the ultimate output. It is described as a PatchGAN discriminator architecture in the above-cited article by P. Isola et al. pertaining to conditional GAN. The discriminator 42 is adapted either to receive CT-pCT slices 86 as inputs and to generate Real/Fake information 87 as outputs ($D_{CT}$), or to receive MR-pMR slices 86 as inputs and to generate Real/Fake information 87 as outputs ($D_{MR}$).

The discriminator 42 is built on layers including:

convolution blocks 881, dedicated to 4×4 Conv2D (Stride 2)+InstanceNorm+Leaky ReLU, a convolution block 882, dedicated to 4×4 Conv2D (Stride 1)+InstanceNorm+Leaky ReLU, a convolution block 883 and having a single filter, dedicated to 1×1 Conv2D (Stride 1)+Sigmoid.

The filters in the first convolution block 881 are 32, and the number of filters is then rising exponentially with each downs ampling—up to 216 filters in the block 882.

In training operation with the first ML framework 31, an MR slice and a CT slice are fed as inputs, and it is ensured that they are coming from a same region of the body of a same patient for sake of enhanced stability and better results. The generator $G_{CT}$ then takes as input the pre-processed MR slice and tries to output its corresponding CT slice. The output pCT is then passed to the discriminator $D_{CT}$, which endeavors to distinguish it from the real CT slice. The generated pseudo CT slice is further fed to the generator $G_{MR}$, which tries to generate an MR slice from it. An L1 distance is then computed between the actual MR and the reconstructed rMR. The same method is followed in the reverse direction, by taking the CT slice as input, generating a pseudo MR slice, comparing it to a real MR slice using the discriminator $D_{MR}$, and then reconstructing back the CT slice and comparing the result rCT to the actual CT slice. Cycle consistency is thus ensured and the need for paired data is eliminated.

The training is e.g. effected by performing stochastic gradient descent with adaptive momentum at a learning rate of $2 \times 10^{-4}$, and a batch size of 1. The choice of the hyperparameters for adaptive momentum may be consistent with the recommendations given by A. Radford, L. Metz and S. Chintala in "Unsupervised representation learning with deep convolutional generative adversarial networks", 2016, arXiv: 1511.06434. The adaptive momentum $\beta_1$ and $\beta_2$ are e.g. set to 0.5 and 0.99 respectively, which prove to yield stable performance.

Considering CT and MR slices noted respectively ct and mr, the objective for the stochastic gradient descent is defined as a weighted sum of an L1 distance between the reconstructed CT, $G_{CT}(G_{MR}(ct))$ and original CT (ct) and an L1 distance between the reconstructed MR, $G_{MR}(G_{CT}(mr))$ and original MR (mr):

$$\mathcal{L}_{rec} = \mathbb{E}_{mr \sim p_{data}(mr)}[\|G_{MR}(G_{CT}(mr)) - mr\|_1] +$$

$$\mathbb{E}_{ct \sim p_{data}(ct)}[\|G_{CT}(G_{MR}(ct)) - ct\|_1] \qquad (1)$$

along with an adversarial loss between the generated CT and original CT, and an adversarial loss between the generated MR and original MR:

$$\mathcal{L}_{adv(CT)} = \mathbb{E}_{ct \sim p_{data}(ct)}[\log D_{DT}(ct)] +$$

$$\mathbb{E}_{mr \sim p_{data}(mr)}[\log(1 - D_{CT}(G_{CT}(mr)))] \qquad (2)$$

$$\mathcal{L}_{adv(MR)} = \mathbb{E}_{mr \sim p_{data}(mr)}[\log D_{MR}(mr)] +$$

$$\mathbb{E}_{ct \sim p_{data}(ct)}[\log(1 - D_{MR}(G_{MR}(ct)))] \qquad (3)$$

An L2 distance is used for the adversarial losses, between the actual label of the slice (1 for real, 0 for fake) and the predicted soft label by the discriminator when optimizing for the discriminator, and the reverse objective (1 for fake, 0 for real) when optimizing for the generator.

This leads to the overall loss:

$$\mathcal{L}_{total} = \mathcal{L}_{adv(CT)} + \mathcal{L}_{adv(MR)} + \lambda \mathcal{L}_{rec} \qquad (4)$$

in which the value of $\lambda$ is chosen to be 10, meaning the reconstruction loss is weighted 10 times more than the adversarial loss. The final optimization goal can then be summed up as:

$$G_{CT}^*, G_{MR}^* = \arg \min_{G_{CT}, G_{MR}} \max_{D_{CT}, D_{MR}} \mathcal{L}_{total} \qquad (5)$$

After having trained 12 different models using this method, i.e. 4 atlases and 3 views each, the results are processed to get the pseudo CTs (post-prediction module 113). In particular, the results are combined from each model (ensembling), which leads to a significant reduction in artefacts overall. Indeed, due to the fact that the pipeline of the first ML framework 31 is completely unsupervised, slicing artefacts are introduced when reconstructing 3D volume from 2D slices. However, since the artefacts are different in each view and on different atlases, combining the results provides the above desirable enhancement.

More precisely, the 3D CTs are reconstructed from the slices output by each trained model in the different views. Then, an inverse warping is performed from the corresponding atlas grids to return to the original MR grid. With all pseudo CTs on the same grid, the volumes are finally scaled to return from the range of −1, 1 back to −1000, 500. A voxel wise median over the 12 volumes is then computed to get the final intensity value at each voxel.

The pseudo CTs generated respectively for all MR images in the original training dataset 271 are then used as targets to perform a deformable registration between the original CT and the pseudo CT, using e.g. the above-cited algorithm by B. Glocker et al. To perform the registration, a sum of absolute differences and a segmentation loss on organ masks with a low regularization are used. The organ masks pertain to rectum and bladder, so that a complete alignment is ensured on the two volumes. Also, a weight ratio of 100:1 is used for segmentation loss and sum of absolute differences. Using this strategy, the CT is successfully aligned to the MR without having to do cross-modality image registration.

Once the registration on the entire original training set 271 is performed and the new paired dataset is generated (the induced training set 22), including the original CTs deformed to match the MRs, the supervised learning phase is started.

2/ Second Phase Implementation (Supervised)

The second phase unit 12 (pre-prediction module 121) proceeds with the preliminary steps in a similar way as the first phase unit 11, while taking as ground truth labels the CT volumes registered to the pseudo CTs at the end of the previous phase. Those registered CTs are rescaled between −1 and 1.

The volumes are registered to four different atlas grids, but for that second phase, the models are only trained on the axial slices instead of all three views. This speeds up significantly the final production pipeline derived from this second phase, since only 4 outputs instead of 12 are computed, while preserving the quality of the results. Indeed, the presence of a supervised strategy entails minimal slicing artefacts, so that a gain obtained by combining multiple views would be relatively small. Also, like for the first phase, one slice out of 8 per volume is randomly selected.

Paired CT-MR slices are thus available for being fed to the learning stage (training module 122).

In advantageous implementations, the previous Cycle-GAN training configuration (i.e. the ML architecture scheme) is kept for the second ML framework 32, despite the fact that the input data are paired. Retaining constraints of the unsupervised first ML framework 31 enhances the generation of realistic organs, even when it is not possible to have them well aligned, which may happen with organs like the intestines or with air pockets inside the rectum.

Figure 15:
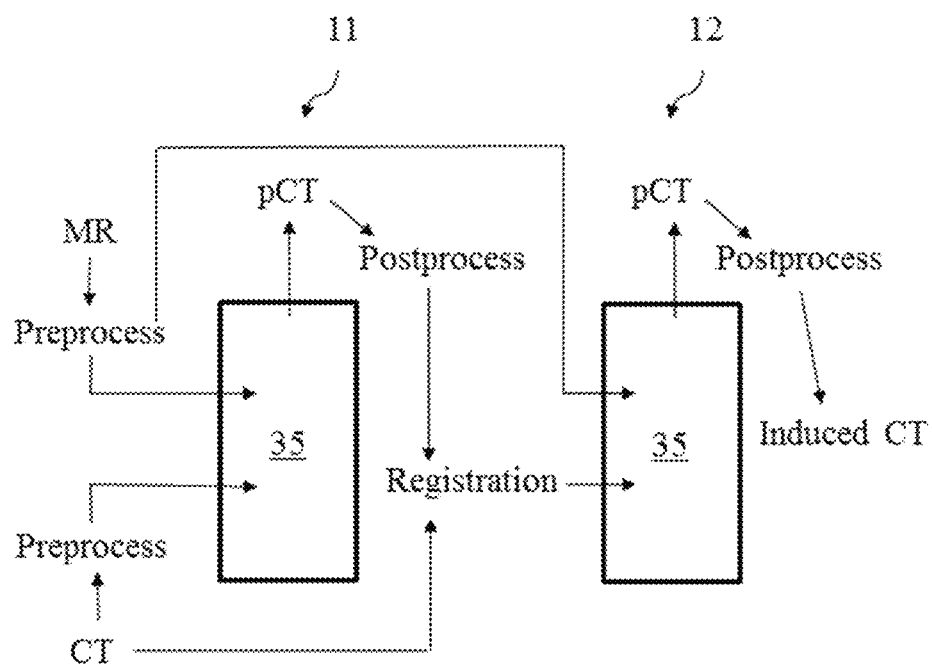
FIG. 15 represents a particular two-phase self-supervised learning pipeline suited to the device for synthesizing images of FIG. 1 as applied to the translation of MR images to CT images, integrating the CycleGAN bidirectional pass workflow of FIGS. 12, 13 and 14, and relevant to the device for treatment planning of FIG. 11.

This leads to a succession of the two phase units 11 and 12, as represented on FIG. 15, in which the CycleGAN framework 35 (FIG. 12) is exploited twice:
  in the first phase unit 11, with the preprocessed MR and CT images derived from the original training set 271 as entries, and with the preprocessed MR and the deformed original CT images (registered to the post-processed induced CT images) as outputs;
  in the second phase unit 12, with the preprocessed MR images and the preprocessed registered CT images as entries, and with the operational trained model 320 as a result, the latter being embodied in the forward pass (MR to CT) of the CycleGAN framework 35 once trained.

The generator 41 and the discriminator 42 (FIGS. 13 and 14) are exploited in this second phase unit 12, too, but the base filters in the generator 41 are reduced from 64 to 32, and in the discriminator 42 from 32 to 16 (X=32). The reduction of the number of filters reduces the memory consumption of the models on the GPU, meaning larger batches of slices can be passed during evaluation, and makes a single forward pass faster, due to reduced computations. This results in overall faster training and evaluation. The reduction in the number of filters is possible without prejudice, since the training is supported by paired images, which makes the problem of modelling the pseudo CT and pseudo MR a lot less complicated.

The supervised learning pipeline of the second phase unit 12 supports the adversarial loss on generated images as described for the first phase unit 11 with an L1 loss against the ground truth label:

$$\mathcal{L}_{pairedL_1} = \mathbb{E}_{mr \sim p_{data}(mr)}[\|G_{MR}(ct)) - mr\|_1] +$$

$$\mathbb{E}_{ct \sim p_{data}(ct)}[\|G_{CT}((mr)) - ct\|_1] \quad (6)$$

and with a local normalized cross-correlation (NCC) loss against the ground truth label, to provide a stronger constraint for generation:

$$\mathcal{L}_{NCC} = \mathbb{E}_{ct \sim p_{data}(ct)}[1 - \sqrt{NCC(ct, G_{CT}(mr))^2}] +$$

$$\mathbb{E}_{mr \sim p_{data}(mr)}[1 - \sqrt{NCC(mr, G_{MR}(ct))^2}] \quad (7)$$

The NCC terms are defined as below, between two images $I:\Omega \mapsto \mathbb{R}$ and $J:\Omega \mapsto \mathbb{R}$, with $\circledast$ designating the convolution operation between an image and a kernel, $W:\Omega_W=[0;K]^2 \mapsto R$ being a kernel of size K such that $\forall u \in_W, W[u] = 1/K^2$:

$$NCC(I, J)^2 = \frac{(IJ \circledast W - (I \circledast W)(J \circledast W))^2}{(I^2 \circledast W - (I \circledast W)^2)(J^2 \circledast W - (J \circledast W)^2)} \quad (8)$$

The final loss function is then given by:

$$\mathcal{L}_{total} = \mathcal{L}_{adv(CT)} + \mathcal{L}_{adv(MR)} + \lambda_1 \mathcal{L}_{rec} +$$

$$\lambda_2(\mathcal{L}_{NCC} + \mathcal{L}_{pairedL_1}) \quad (9)$$

where a value of 10 is e.g. used for both $\lambda_1$ and $\lambda_2$, i.e. for each of the non-adversarial losses (L1, NCC and reconstruction). The optimization objective can still be defined by equation (5), using the definition of equation (9) for $\mathcal{L}_{total}$.

Taking account of the cycle consistency loss (reconstruction loss) along with the adversarial loss reinforces the model to possibly still produce anatomical accurate and realistic looking outputs where regions cannot be completely aligned.

This unsupervised setting is trained with stochastic gradient descent optimization with adaptive momentum, all training parameters being possibly the same as for the first phase.

Once the four models are obtained on the four atlas grids, the post-prediction operations can be carried out (post-prediction module 123): the 3D volume is reconstructed from the 2D slices output by the models, an inverse warping is performed to get back to the original MR grid, the values are scaled back to −1000 and 500, and the mean of the four volumes is taken to get the final output (ensembling).

3/ Production Pipeline

During the training phase, 64 different deep learning models are been trained: one training per view per atlas during the first phase and one training per atlas during the second phase, each training with two generators and two discriminators. However, once the training is complete, only 4 out of the 64 models are required for the final pseudo CT generation: the 4 MR to CT generators of the second phase, i.e. one per atlas.

Figure 16:
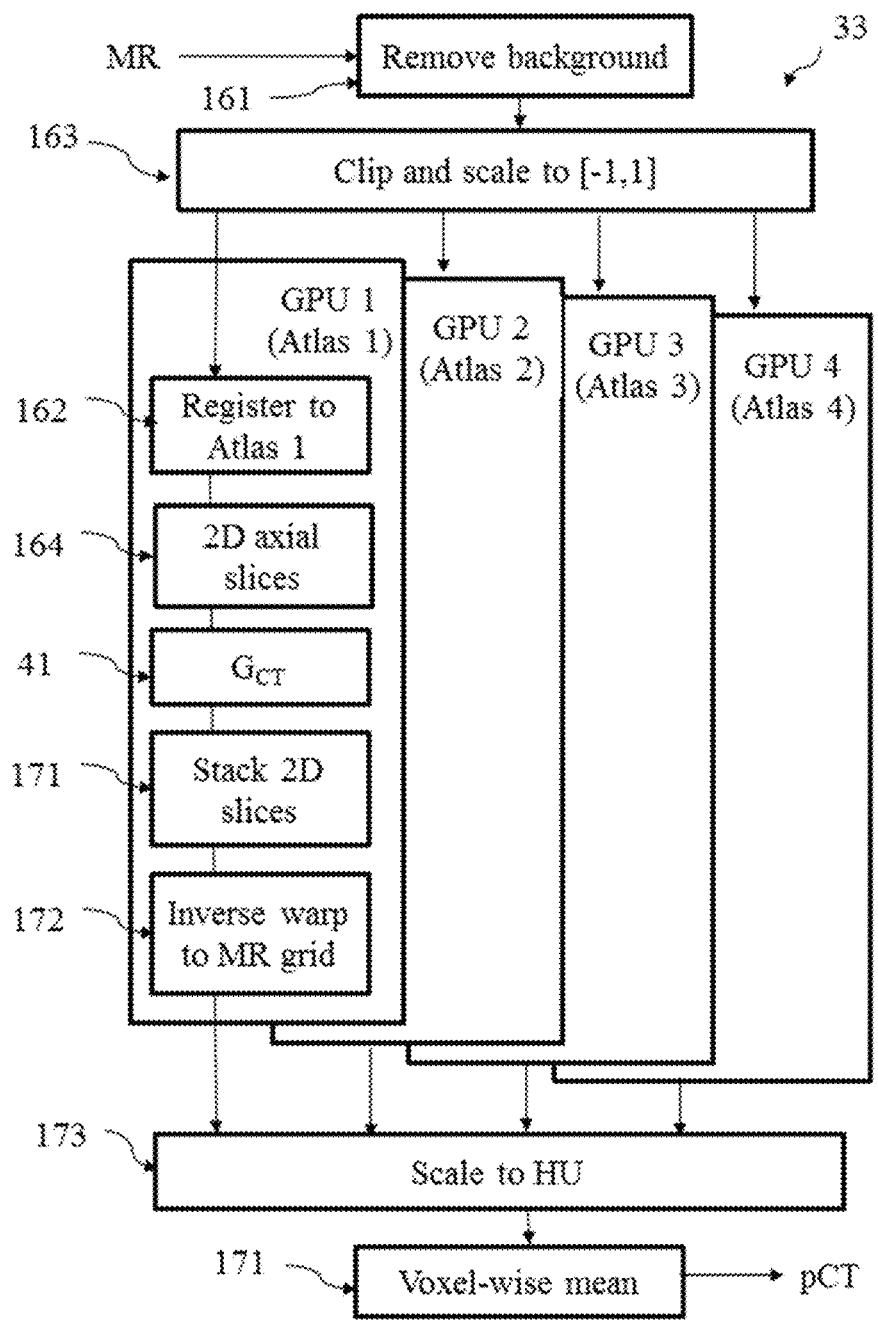
FIG. 16 represents a production pipeline for generating synthetic CT images from MR images, derived from the self-supervised learning pipeline of FIG. 15 and relevant to the device for treatment planning of FIG. 11.

In operation on a final production pipeline 33, as illustrated on FIG. 16 and in relation with the previous explanations about the production device 13 (FIGS. 2, 3, 6), the operational MRs images 281 are taken as input, the external contour is computed using an external contouring algorithm, and the artefacts outside the body are removed by setting the values of all outside voxels to 0. The MRI is then clipped at 99.8 percentile and scaled between −1 and 1. This is followed by an affine registration between the MR and the atlas CT for the four atlases. The axial slices from each of the four registered MRs are then passed to the four models in parallel on different GPUs for computation. The results are stacked onto a 3D volume and each of those pseudo CTs is inverse warped onto the original grid. Finally, the voxelwise mean over the four volumes is taken to get the output pseudo CT 282.

The algorithm was implemented on a machine with GPUs marketed by Nvidia under the trade name GeForce GTX 1080 Ti (each GPU including 3584 CUDA cores—for Compute Unified Device Architecture—and 11 GB GDDRSX memory). When computing pseudo CT from a given high resolution MRI volume (0.5 mm, 0.5 mm, 0.5 mm), the algorithm took on average 60 seconds.

4/ Application Results

For sake of application illustration, a total of 205 CT, T2 MRI pairs taken from 43 patients are selected for training and evaluation. Out of those 205 data samples (i.e. volumes), 43 samples are separated out for algorithm evaluation and the remaining 162 samples are devoted to training and validation, while ensuring that no patient is present in both the training and evaluation sets. The CT and T2 MRI scans are taken on scanners commercialized by Philips respectively under the trade names Brilliance Big Bore and Marlin 1.5 MRI. All MR images have high resolution, with the minimum and maximum slice thickness being 0.5 mm and 1.2 mm respectively.

Following the computations as detailed above, it is reported on the held-out test set of 43 volumes a mean absolute error (MAE) of 33.1±7.4 HU between the synthetic CT obtained with the above described implementation (corresponding to the target part of the induced training set 22) and a directly registered CT.

Figure 17:
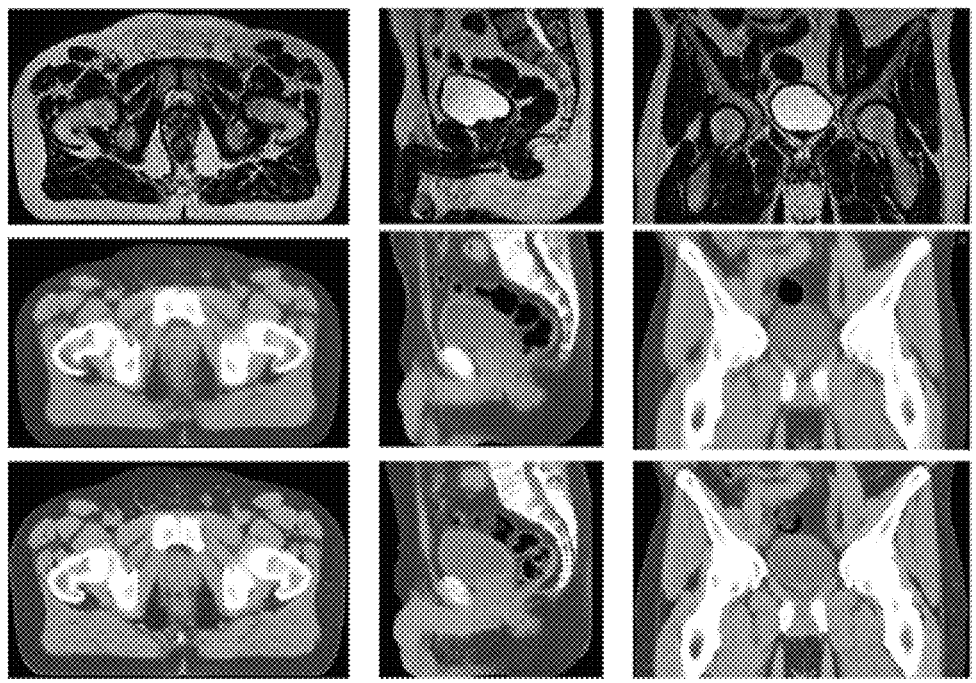
FIG. 17 comprises photographs showing sample results of synthetic CT generation from T2 pelvic MRI using an algorithm compliant with the self-supervised learning pipeline of FIG. 15, displaying input MRI in three views (top row), as well as respectively corresponding intermediate CT images generated in the first (unsupervised) phase of the learning pipeline (middle row), and generated final synthetic CT images (bottom row)
Figure 18:
FIG. 18 comprises photographs showing an original CT (left), as well as corresponding intermediate CT image generated in the first (unsupervised) phase of the learning pipeline (middle) and generated final synthetic CT image (right), using an algorithm compliant with the self-supervised learning pipeline of FIG. 15.

On the photos of FIG. 17, input T2 pelvis MRI (top row), corresponding unsupervised weak priors generated in the first phase (intermediate induced CT, middle row) and the final synthetic CTs (bottom row) can be visualized in three views. Also, on the photos of FIG. 18, similitudes between an original CT (left), the corresponding unsupervised weak prior (middle) and the final synthetic CT (right) can be observed.

Figure 19:
FIG. 19 comprises photographs showing automatic contouring of organs at risk on a generated synthetic CT image, as obtained with a device for treatment planning compliant with FIG. 11 including the production pipeline of FIG. 16.

The running of operational MR images with the production pipeline 33 enables, as visible on FIG. 19, the automatic contouring or organs at risk on generated pseudo CTs.

In a variant embodiment, the second ML framework 32 relies on a Conditional GAN (cGAN) learning pipeline instead of a paired CycleGAN, as disclosed notably in the above-cited article by P. Isola et al. and known under the name pix2pix. With the same 205 CT, T2 MRI pairs and experimental conditions, this leads to an MAE of 35.40 HU between the synthetic CT and a directly registered CT.

More comparison details between CycleGAN and cGAN in the second phase are provided in Table I regarding various organs.

TABLE I

Compared organ-wise MAE with CycleGAN and cGAN for second phase

| Organ | Mean Absolute Error (HU) Paired CycleGAN | Mean Absolute Error (HU) Conditional GAN |
|---|---|---|
| Anal Canal | 27.45 | 21.89 |
| Bladder | 15.05 | 16.96 |
| CTVN Prostate | 33.51 | 33.96 |
| Left Femoral Head | 51.27 | 53.45 |
| Left Iliac | 58.50 | 63.43 |
| Medullary Canal | 33.80 | 39.50 |
| Penile Bulb | 14.98 | 13.60 |
| Prostate | 19.79 | 18.41 |
| Rectum | 104.19 | 97.33 |
| Right Femoral Head | 54.64 | 57.37 |
| Right Iliac | 60.89 | 67.40 |
| Seminal Vesicle | 33.19 | 33.15 |
| Spinal Cord | 27.82 | 35.44 |
| Overall | 33.10 | 35.40 |

Implementing Apparatus

Figure 20:
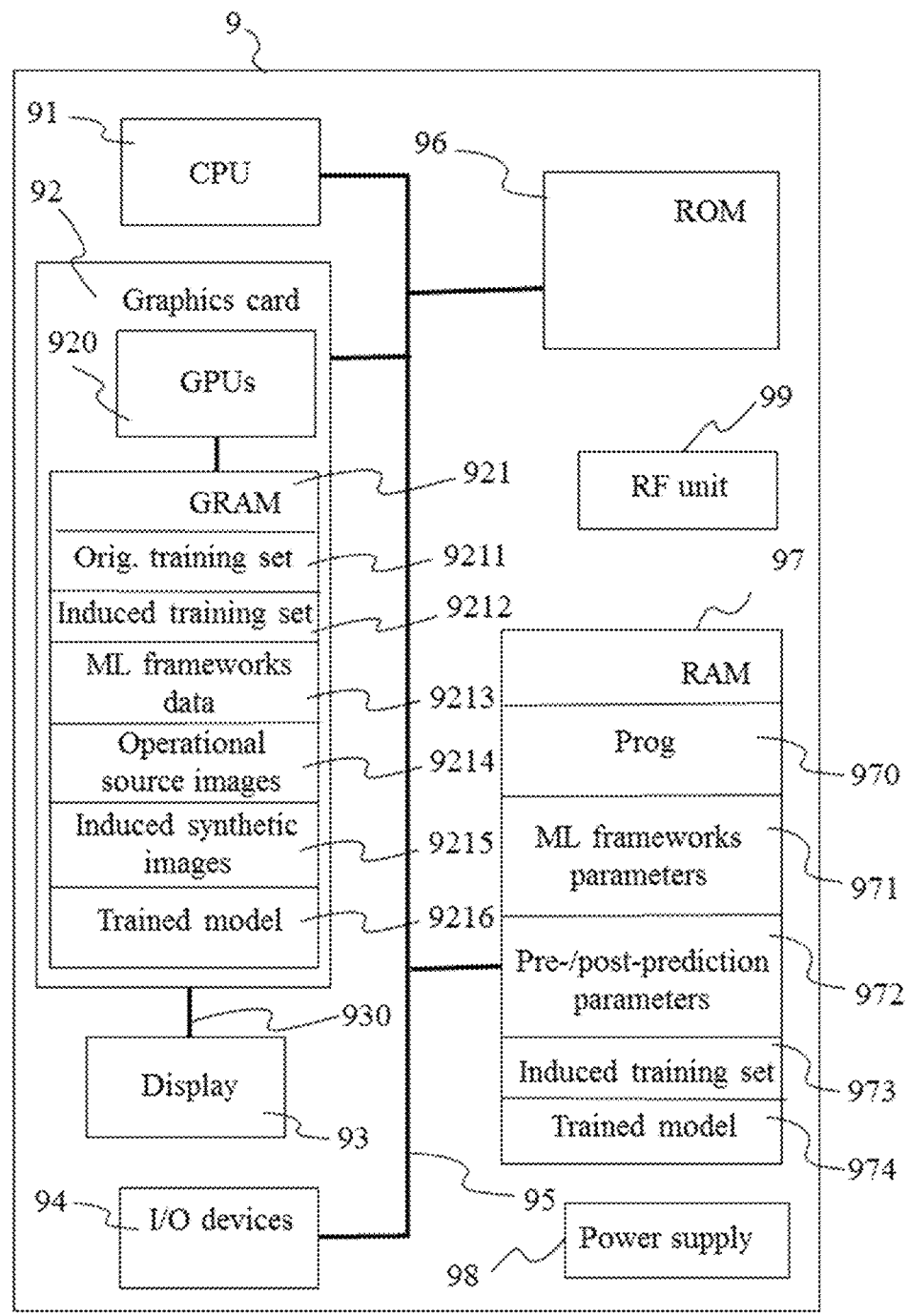
FIG. 20 diagrammatically shows an apparatus integrating the functions of the device for synthesizing images of FIG. 1 and of the production device of FIG. 2.

A particular apparatus 9, visible on FIG. 20, is embodying the devices 1 and 13 as described above. It corresponds for example to a mainframe computer, a workstation, a laptop, a tablet, a smartphone, or a head-mounted display (HMD).

That apparatus 9 is suited to providing a trained model from an original training set in the above described self-supervised way, as well as to running production of induced target images from operational source images based on that trained model. It comprises the following elements, connected to each other by a bus 95 of addresses and data that also transports a clock signal:

- a microprocessor 91 (or CPU);
- a graphics card 92 comprising several Graphical Processing Units (or GPUs) 920 and a Graphical Random Access Memory (GRAM) 921; the GPUs are quite suited to repeated computations on the data samples, due to their highly parallel structure;
- a non-volatile memory of ROM type 96;
- a RAM 97;
- one or several I/O (Input/Output) devices 94 such as for example a keyboard, a mouse, a trackball, a webcam; other modes for introduction of commands such as for example vocal recognition are also possible;
- a power source 98; and
- a radiofrequency unit 99.

According to a variant, the power supply 98 is external to the apparatus 9.

The apparatus 9 also comprises a display device 93 of display screen type directly connected to the graphics card 92 to display synthesized target images calculated and composed in the graphics card. The use of a dedicated bus 930 to connect the display device 93 to the graphics card 92 offers the advantage of having much greater data transmission bitrates and thus reducing the latency time for the displaying of images composed by the graphics card, e.g. for ML representations. According to a variant, a display device is external to apparatus 9 and is connected thereto by a cable or wirelessly for transmitting the display signals. The apparatus 9, for example through the graphics card 92, comprises an interface for transmission or connection adapted to transmit a display signal to an external display means such as for example an LCD or plasma screen or a video-projector. In this respect, the RF unit 99 can be used for wireless transmissions.

It is noted that the word "register" used hereinafter in the description of memories 97 and 921 can designate in each of the memories mentioned, a memory zone of low capacity (some binary data) as well as a memory zone of large capacity (enabling a whole program to be stored or all or part of the data representative of data calculated or to be displayed). Also, the registers represented for the RAM 97 and the GRAM 921 can be arranged and constituted in any manner, and each of them does not necessarily correspond to adjacent memory locations and can be distributed otherwise (which covers notably the situation in which one register includes several smaller registers).

When switched-on, the microprocessor 91 loads and executes the instructions of the program contained in the RAM 97.

The random access memory 97 comprises notably:
in a register 970, the operating program of the microprocessor 91;
in a register 971, parameters relevant to the first ML framework 31 and second ML framework 32;
in a register 972, the pre-prediction and post-prediction parameters;
in a register 973, the induced training set 22;
in a register 974, the trained model 320.

Algorithms implementing the steps of the method specific to the present disclosure and described above are stored in the memory GRAM 921. When switched on and once the parameters 971 to 974 are loaded into the RAM 97, the graphic processors 920 of graphics card 92 load appropriate information and parameters into the GRAM 921 and execute the instructions of algorithms in the form of microprograms.

The random access memory GRAM 921 comprises notably:
in a register 9211, the original training set 21;
in a register 9212, the induced training set 22;
in a register 9213, data associated the first ML framework 31 and second ML framework 32;
in a register 9214, the operational source images 231;
in a register 9215, the induced synthetic images 232;
in a register 9216, the trained model 320.

As will be understood by a skilled person, the presence of the graphics card 92 is not mandatory, and can be replaced with entire CPU processing and/or simpler visualization implementations.

In variant modes, the apparatus 9 may include only the functionalities of the device 1 for synthesizing images, or conversely be relevant to the device 10 for treatment planning and further encompass the functionalities of the contouring module 18 and possibly also of the module 19 for tissue property determination. In addition, the device 1 and the device 13 may be implemented differently than a standalone software, and an apparatus or set of apparatus comprising only parts of the apparatus 9 may be exploited through an API call or via a cloud interface.

The invention claimed is:

1. A device for synthesizing images from a source imaging modality to a target imaging modality through unsupervised machine learning, on the basis of an original training set of unaligned original source images compliant with the source imaging modality and original target images compliant with the target imaging modality, said device comprising:
at least one input adapted to receive the original training set,
at least one processor configured for training a first machine learning architecture through an unsupervised first learning pipeline applied to the original training set, so as to generate a trained model of the first machine learning architecture, adapted to receive images compliant with the source imaging modality and to yield respectively associated images compliant with the target imaging modality, and representations of a plurality of said original source images compliant with the target imaging modality, called induced target images,
wherein said at least one processor is configured for training a second machine learning architecture through an at least partly supervised second learning pipeline applied at least to an induced training set of aligned image pairs, each of said aligned image pairs comprising a first item corresponding to one of said original source images, called a kept source image, and a second item corresponding to the induced target image associated with said kept source image, so as to generate a trained model of the second machine learning architecture, adapted to receive images compliant with the source imaging modality and to yield respectively associated images compliant with the target imaging modality,
said device further comprising:
at least one output adapted to produce at least part of said trained model of the second machine learning architecture, so as to carry out image syntheses from the source imaging modality to the target imaging modality.

2. The device for synthesizing according to claim 1, wherein said original training set includes unaligned image pairs of the original source images and target images, and said at least one processor is configured for training said first machine learning architecture through said first learning pipeline by jointly dealing with said original source and target images of each of said unaligned image pairs, and for generating the second item of at least one of said aligned image pairs associated with one of the original source images belonging to one of said unaligned image pairs by aligning the original target image associated with said original source image to the induced target image associated with said original source image.

3. The device for synthesizing according to claim 1, wherein the second machine learning architecture is more efficient than the first machine learning architecture in a production phase.

4. The device for synthesizing according to claim 3, wherein the first and second machine learning architectures comprising weights and biases, the second machine learning architecture is similar to the first machine learning architecture, subject to a reduction of numbers of said weights and biases.

5. The device for synthesizing according to claim 1, wherein said first machine learning architecture and said first learning pipeline are together bidirectional and cycle consistent.

6. The device for synthesizing according to claim 1, wherein said second machine learning architecture is suited to unsupervised learning and said second learning pipeline involves a joint minimization of at least one term ($\mathcal{L}_{adv(ct)}$, $\mathcal{L}_{adv(MR)}$, $\mathcal{L}_{rec}$) representative of said unsupervised learning and at least one term ($\mathcal{L}_{pairedL_1}$, $\mathcal{L}_{NCC}$) representative of mismatches between said aligned image pairs and intermediate approximations of said aligned image pairs in said joint minimization.

7. The device for synthesizing according to claim 6, wherein said second machine learning architecture and said second learning pipeline are together bidirectional and cycle consistent.

8. The device for synthesizing according to claim 1, wherein the trained models generated by training the first and second machine learning architectures are deterministic.

9. The device for synthesizing according to claim 1, wherein each of said first and second machine learning architectures includes at least one generative adversarial network comprising a generator network based on a fully convolutional network.

10. The device for synthesizing according to claim 1, wherein said at least one processor is configured for preprocessing said original training set by commonly registering said original source images and target images to at least two reference image spaces, independently training said first machine learning architecture on said respective reference image spaces so as to obtain instances of said induced target images associated with said respective reference image spaces, and combining said instances into said induced target images.

11. The device for synthesizing according to claim 1, wherein said original source images and target images being defined in an overall image space comprising at least two image subspaces, said image subspaces being selected among channel spaces and multidimensional spaces, said at least one processor is configured for training said first machine learning architecture on said image subspaces corresponding to said original training set, so as to obtain instances of said induced target images respectively associated with said image subspaces, combining said instances into said induced target images, and training said second machine learning architecture on a reduced number of said image subspaces corresponding to said induced training set.

12. The device for synthesizing according to claim 1, wherein said images being medical images, one of said source imaging modality and said target imaging modality is magnetic resonance imaging and the other of said source imaging modality and said target imaging modality is computed tomography imaging.

13. A device for treatment planning comprising a device for translating medical images, wherein said device for translating is a device for synthesizing images compliant with claim 12, said device for synthesizing being adapted to translate magnetic resonance images to computed tomography images, and in that said device for treatment planning comprises:
- at least one input adapted to receive operational magnetic resonance images, said device for synthesizing being adapted to translate said operational magnetic resonance images to synthetic computed tomography images,
- at least one processor configured for automatically contouring organs in said synthetic computed tomography images,
- at least one output adapted to produce organ contours from said contouring with a view to radiation dose delivery.

14. A method for synthesizing images from a source imaging modality to a target imaging modality through unsupervised machine learning, on the basis of an original training set of unaligned original source images compliant with the source imaging modality and original target images compliant with the target imaging modality, said method comprising:
- receiving the original training set,
- training by at least one processor a first machine learning architecture through an unsupervised first learning pipeline applied to the original training set, so as to generate a trained model of the first machine learning architecture, adapted to receive images compliant with the source imaging modality and to yield respectively associated images compliant with the target imaging modality, and representations of a plurality of said original source images compliant with the target imaging modality, called induced target images,
- wherein said method comprises training by said at least one processor a second machine learning architecture through an at least partly supervised second learning pipeline applied at least to an induced training set of aligned image pairs, each of said aligned image pairs comprising a first item corresponding to one of said original source images, called a kept source image, and a second item corresponding to the induced target image associated with said kept source image, so as to generate a trained model of the second machine learning architecture, adapted to receive images compliant with the source imaging modality and to yield respectively associated images compliant with the target imaging modality,
- said method further comprising producing at least part of said trained model of the second machine learning architecture, so as to carry out image syntheses from the source imaging modality to the target imaging modality,
- said method for synthesizing being advantageously executed by a device for synthesizing according to claim 1.

15. A computer program comprising software code stored on a non-transitory program storage device readable by computer adapted to perform a method for synthesizing according to claim 14 when it is executed by a processor.

* * * * *